(12) United States Patent
Allphin et al.

(10) Patent No.: US 9,555,017 B2
(45) Date of Patent: *Jan. 31, 2017

(54) METHODS OF MAKING A MIXTURE OF SALTS OF GAMMA-HYDROXYBUTYRATE

(71) Applicant: Jazz Pharmaceuticals Ireland Limited, Dublin (IE)

(72) Inventors: Clark P. Allphin, Los Altos, CA (US); Michael DesJardin, Aptos, CA (US)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,384

(22) Filed: Aug. 7, 2015

(65) Prior Publication Data

US 2016/0058720 A1 Mar. 3, 2016

Related U.S. Application Data

(63) Continuation of application No. 14/045,673, filed on Oct. 3, 2013, now Pat. No. 9,132,107, which is a continuation of application No. 13/739,886, filed on Jan. 11, 2013, now Pat. No. 8,591,922.

(60) Provisional application No. 61/737,695, filed on Dec. 14, 2012.

(51) Int. Cl.
  *A61K 31/19* (2006.01)
  *A61K 31/554* (2006.01)

(52) U.S. Cl.
  CPC ............. *A61K 31/19* (2013.01); *A61K 31/554* (2013.01)

(58) Field of Classification Search
  CPC ... A61K 31/19; A61K 31/554; A61K 2300/00
  USPC ........................................................ 514/557
  See application file for complete search history.

(56) References Cited

U.S. PATENT DOCUMENTS

| 4,374,441 | A | 2/1983 | Carter et al. |
| 4,393,236 | A | 7/1983 | Klosa |
| 4,738,985 | A | 4/1988 | Kluger et al. |
| 4,983,632 | A | 1/1991 | Gessa et al. |
| 5,380,937 | A | 1/1995 | Koehler et al. |
| 5,594,030 | A | 1/1997 | Conte et al. |
| 5,753,708 | A | 5/1998 | Koehler et al. |
| 5,840,331 | A | 11/1998 | Van Cauter et al. |
| 5,990,162 | A | 11/1999 | Scharf |
| 6,436,998 | B1 | 8/2002 | Cacciaglia et al. |
| 6,472,431 | B2 | 10/2002 | Cook et al. |
| 6,495,598 | B1 | 12/2002 | Yoneda et al. |
| 6,780,889 | B2 | 8/2004 | Cook et al. |
| 7,015,200 | B2 | 3/2006 | Mamelak et al. |
| 7,262,219 | B2 | 8/2007 | Cook et al. |
| 7,851,506 | B2 | 12/2010 | Cook et al. |
| 8,263,650 | B2 | 9/2012 | Cook et al. |
| 8,324,275 | B2 | 12/2012 | Cook et al. |
| 8,591,922 | B1 | 11/2013 | Allphin et al. |
| 8,772,306 | B1 | 7/2014 | Eller |
| 8,901,173 | B2 | 12/2014 | Allphin et al. |
| 8,952,029 | B2 | 2/2015 | Eller |
| 9,050,302 | B2 | 6/2015 | Eller |
| 9,132,107 | B2 | 9/2015 | Allphin et al. |
| 2005/0113366 | A1 | 5/2005 | Bourguignon et al. |
| 2007/0270491 | A1 | 11/2007 | Cook et al. |
| 2008/0293698 | A1 | 11/2008 | Johnson |
| 2011/0034727 | A1 | 2/2011 | Luchi et al. |
| 2011/0039929 | A1 | 2/2011 | Cook et al. |
| 2011/0111027 | A1 | 5/2011 | Rourke et al. |
| 2012/0020833 | A1 | 1/2012 | Cook et al. |
| 2012/0202880 | A1 | 8/2012 | Cook et al. |

FOREIGN PATENT DOCUMENTS

| EP | 0235408 A1 | 9/1987 |
| EP | 0344704 A1 | 6/1989 |
| EP | 0635265 A1 | 7/1994 |
| EP | 0616804 A1 | 9/1994 |
| EP | 1140061 B1 | 10/2001 |
| GB | 922029 | 3/1963 |
| JP | 57-042651 | 3/1982 |
| JP | 04-049212 | 2/1992 |
| JP | 05-508422 | 11/1993 |
| WO | 9640105 A1 | 12/1996 |

OTHER PUBLICATIONS

Berner, Jon E., "A Case of Sodium Oxybate Treatment of Tardive Dyskinsela and Bipolar Diorder," J. Clin. Psychiatry, 2008, 69: 862.
Snead, O. Carter et al., "Ontogeny of Gamma-Hydroxybutyric Acid. I. Regional Concentration in Developing Rat, Money and Human Brain," Brain Res., 1981, 227(4): 579-589.
Scharf, Martin B., et al., The Effects of Sodium Oxybate on Clinical Symptoms and Sleep Patterns in Patients with Fibromyalgia, J. Rheumatol, 2003, 30(5): 1070-1074.
Russel, I. Jon, et al., "Sodium Oxybate Relieves Pain and Improves Function in Fibromyaligia Syndrome," Arthritis. Rheum., 2009, 60: 299-309.
Ondo, William G., et al., "Sodium Oxybate for Excessive Daytime Sleepiness in Parkinson Disease," Arch. Neural., 2008, 65(10): 1337-1340.
Frucht, S.J., et al., "A Single-Blind, Open-Label Trial of Sodium Oxybate for Myoclonus and Essential Tremor," Neurology, 2005, 65: 1967-1970.
Ladinsky, Herbert, et al., "Mode of Action of Gamma-Butyrolactone on the Central Cholinergic System," Naunyn-Schmiedeberg's Arch. Pharmacal., 1983, 322: 42-48.
Lammers, G.J., et al., "Gammahydroxybutyrate and Narcolepsy: A Double-Blind Placebo-Controlled Study," Sleep, 1993, 16(3): 216-220.

(Continued)

*Primary Examiner* — Yanzhi Zhang
(74) *Attorney, Agent, or Firm* — Jones Day

(57) ABSTRACT

Provided herein are pharmaceutical compositions and formulations comprising mixed salts of gamma-hydroxybutyrate (GHB). Also provided herein are methods of making the pharmaceutical compositions and formulations, and methods of their use for the treatment of sleep disorders such as apnea, sleep time disturbances, narcolepsy, cataplexy, sleep paralysis, hypnagogic hallucination, sleep arousal, insomnia, and nocturnal myoclonus.

25 Claims, 1 Drawing Sheet

(56) References Cited

OTHER PUBLICATIONS

Snead, O. Carter, "Gamma-Hydroxybutyrate Model of Generalized Absence Seizures: Further Characterization and Comparison with Other Absence Models," Epilepsia, 1988, 29(4): 361-368.

Lapierre, O., et al., "The Effect of Gamma-Hydroxybutyrate on Nocturnal and Diurnal Sleep of Normal Subjects: Further Considerations on REM Sleep-Triggering Mechanisms," Sleep, 1990, 13(1): 24-30.

Laborit, H., "Gamma-Hydroxybutyrate, Succinic Semialdehyde and Sleep," Laboratoire d'Eutonologie, 1973, 8: 257-274.

United States District Court, "Order," Jazz Pharmaceuticals, Inc. v. Roxane Laboratories, Inc., Markman Hearing, No. 10-6108 (ES), (Sep. 14, 2012), 1 pg.

Arena, C., et al., "Absorption of Sodium Gamma-Hydroxybutyrate and its Prodrug Gamma-Butyrolactone: Relationship Between In Vitro Transport and In Vivo Absorption," Journal of Pharmaceutical Sciences, 1980, 69(3): 356-358.

Bédard, M.A., et al., "Nocturnal Gamma-Hydroxybutyrate—Effect on Periodic Leg Movements and Sleep Organization of Narcoleptic Patients", Clin Neuropharmacol., 1989, 12(1): 29-36.

Berthier, M, et al., "Possible Involvement of a Gamma-Hydroxybutyric Acid Receptor in Startle Disease", Acta Paediatr, 1994, 83(6): 678-680.

Broughton, Roger, et al., "The Treatment of Narcolepsy-Cataplexy with Nocturnal Gamma-Hydroxybutyrate", Le Journal Canadien des Sciences Neurologiques, 1979, 6(1): 285-289.

Snead, O. Carter, et al., "Ontogeny of Gamma-Hydroxybutyric Acid. Regional Concentration in Developing Rat, Monkey and Human Brain", Brain Res., 1981, 227(4): 579-589.

Ferrara, S.D., et al., "Pharmacokinetics of Gamma-Hydroxybutyric Acid in Alcohol Dependent Patients After Single and and Repeated Oral Doses", Br. J. Clin. Pharmaca., 1992, 34(3): 231-235.

Gallimberti, L., et al., "Gamma-Hydroxybutric Acid in the Treatment of Alcohol Dependence: A Double-Blind Study", Alcohol Clin. Exp. Res., 1992, 16(4): 673-676.

Gallimberti, L., et al., "Gamma-hydroxybutyric Acid for Treatment of Alcohol Withdrawal Syndrome", Clinical Pharmacology, 1989, 2(8666): 787-789.

Scrima, L, et al., "Efficacy of Gamma-Hydroxybutyrate Versus Placebo in Treating Narcolepsy-Cataplexy: Double-Blind Subjective Measures", Biol. Psychiatry, 1989, 26(4): 331-343.

Gessa, Gian Luigi, et al., "Gamma-hydroxybutyric acid (GHB) for treatment of ethanol dependence", European Neuropsychopharmacology, 1993, 3(3): 224-225.

Gessa, G.L., "Gamma-Hydroxybutyric Acid in the Treatment of Alcohol Dependence", Clin. Neuropharm., 15 Suppl. 1, Pt. A, (1992), 303a-304a.

Grove-White, I.G., et al., "Effect of Methohexitone, Diazepam and Sodium 4-Hydroxybutyrate on Short-Term Memory", Brit. J. Anaesth., 1971, 43: 113-116.

Grove-White, I.G., et al., "Critical Flicker Frequency after Small Doses of Methohexitone, Diazepam and Sodium 4-Hydroxybutyrate", Brit. J. Anaesth, 1971, 43(2): 110-112.

Hasenbos, M A, "Anaesthesia for bullectomy. A technique with spontaneous ventilation and extradural blockade", Anaesthesia, 1985, 40(10): 977-980.

Hoes, M.J.A.J.M., et al., "Gamma-hydroxybutyric acid as hypnotic. Clinical and pharmacokinetic evaluation of gamma-hydroxybutyric acid as hypnotic in man", Encephale, 1980, 6(1): 93-99.

Scrima, Lawrence, et al., "The Effects of Gamma-Hydroxybutyrate on the Sleep of Narcolepsy Patients: A Double Blind Study", Sleep, 1990, 13(6): 479-490.

Sériès, F., et al., "Effects of Enhancing Slow-Wave Sleep by Gamma-Hydroxybutyrate on Obstructive Sleep Apnea", Am. Rev. Respir. Dis., 1992, 145(6): 1378-1383. Li.

United States District Court, "Opinion," Jazz Pharmaceuticals, Inc. v. Roxane Laboratories, Inc., Markman Hearing, No. 10-6108 (ES), (Sep. 14, 2012), 43 pg.

Stock, Günter, et al., "Increase in Brain Dopamine after Axotomy or Treatment with Gammahydroxybutyric Acid Due to Elimination of the Nerve Impulse Flow", Naunyn-Schmiedeberg's Arch. Pharmacal., 1973, 278(4): 347-361.

Strong, A. J., "Gamma-Hydroxybutyric Acid and Intracranial Pressure", The Lancet, 1984, 1(8389): 1304.

Van Den Bogert, et al., "Placentatransfer of 4-Hydroxybutyric Acid in Man", Anaesthesiology and Intensive Care Medicine, 1978, 110: 55-64.

Vickers, M.D., "Gammahydroxybutyric Acid", Int. Anesth. Clinic, 1969, 7(1): 75-89.

Yamada, Y., et al., "Effect of Butyrolactone and Gamma-Hydroxybutyrate on the EEG and Sleep Cycle in Man", Electroenceph. clin. Neurophysiol., 1967, 22: 558-562.

Ferris, Trevor J., et al., "Synthesis, characterisation and detection of gamma-hydroxybutyrate salts", Forensic Science International, 2012, 216: 158-162.

Lynch, M., "Malic Acid", The Handbook of Pharmaceutical Excipients, 2nd Ed., 1994, 633: 285-286.

Greekwrench et al., "Titel: Does anyone know why Jazz chose to make sodium oxybate?," published Sep. 14, 2010; downloaded from http://www.talkaboutsleep.com/message-boards/topic/does-anybody-know-why-jazz-chose-to-make-sodium-oxybate/#sthash.no0PSCkL.dpuf on Jan. 21, 2015.

Fides, "Solutions of 4-hydroxybutyric acid salts for injection," Chem Abstract ES302338, Laboratorio M. Cuatecases, S.A., 2011, 2 pp.

United States Pharmacopeia (USP), Pharmaceutic Ingredients, 23/NF18, 1995, p. 2205.

Morrison, Robert T., et al., "Organic Chemistry", Chapter 20: "Functional Derivatives of Carboxylic Acids," 3rd Edition, 1973, pp. 658-700.

Roth, R. H., et al., "Gamma-Butyrolactone and Gamma-Hydroxybutyric Acid—II. The Pharmacologically Active Form", J. Neuropharmacol. 1966, 5: 421-428.

Gerra, G., et al., "Flumazenil effects on growth hormone response to gammahydroxybutyric acid", Int Clin Psychopharmacol., 1994, 9(3): 211-215.

Neuman, Ariel, "GHB's Path to Legitimacy: An Administrative and Legislative History of Xyrem", paper submitted to Harvard Law School, 2004, 1-39.

Tunnicliff, Godfrey, "Sites of Action of Gamma-Hydroxybutyrate (GHB)—A Neuroactive Drug with Abuse Potential", Clinical Toxicology, 1997, 35(6): 581-590.

European Patent Office, European Search Report for European Application Serial No. 03075658.9, mailed Apr. 11, 2003, 5 pg.

Jurkovich, Patti, Amendment filed in response to Written Opinion, International Application Serial No. PCT/US99/30740, filed Feb. 16, 2001, 9 pg.

International Searching Authority, International Search Report for International Application Serial No. PCT/US99/30740, mailed Jul. 21, 2000, 1 pg.

Jazz Pharmaceuticals, Inc., "XYREM® (sodium oxybate) oral solution Prescribing Information," XYREM® US Package Insert available at httn://www.xvrem.com/xyrem-Qi.Qdf (downloaded May 3, 2013).

Erowid, "Gamma-hydroxybutyrate (GHB) Basic Synthesis Procedure," http://www.crowid.ondchemicals/ghb/ghbsvnthcsis.shtm (as downloaded on Aug. 8, 2013).

Lee, C.R., "Evidence for the Beta-Oxidation of Orally Administered 4-Hydroxybutyrate in Humans", Biochemical Medicine, 1977, 17(3): 284-291.

Lettieri, John, et al., "Improved Pharmacological Activity via Pro-Drug Modification: Comparative Pharmacokinetics of Sodium Gamm-Hydroxybutyrate and Gamma-Butyrolactone", Research Communications in Chemical Pathology and Pharmacology, 1978, 22(1): 107-118.

Mamelak, Mortimer, "Gammahydroxybutyrate: An Endogenous Regulator of Energy Metabolism", Neuroscience and Biobehavioral Reviews, 1989, 13(4): 187-198.

Mamelak, M., et al., "Sleep-Inducing Effects of Gammahydroxybutyrate", The Lancet, 1973, 2(7824): 328-329.

(56) References Cited

OTHER PUBLICATIONS

Mamelak, Morty, et al., "The Effects of Gamma-Hydroxybutyrate on Sleep", Biological Psychiatry, 1977, 12(2): 273-288.
Nema, Sandeep, et al., "Excipients and Their Use in Injectable Products", PDA J. Pharm. Sci. Technol, 1997, 51(4): 166-171.
Palatini, P., et al., "Dose-Dependent Absorption and Elimination of Gamma-Hydroxybutyric Acid in Healthy Volunteers", Eur. J. Clin. Pharmacal., 1993, 45(4): 353-356.
Roth, Robert H., et al., "Gamma-Butyrolactone and Gamma-Hydroxybutyric Acid—I, Distribution and Metabolism", Biochemical Pharmacology, 1966, 15: 1333-1348.
Scharf, M.B., et al., "The Effects and Effectiveness of Gamma-Hydroxybutyrate in Patients with Narcolepsy", J. Clin. Psychiatry, 1985, 46(6): 222-225.
Scrima, L. et al., "Effect of Gamma-Hydroxybutyrate on a Patient with Obstructive Sleep Apnea," Sleep Research, Abstract, 1987, 16: 137.
Suner, S., et al., "Pediatric Gamma Hydroxybutyrate Intoxication", Acad. Emerg. Med., 1997, 4(11): 1041-1045.
Scrima, et al., "Effect of High Altitude on a Patient with Obstructive Sleep Apnea", Sleep Research, Abstract, 1987, 16: 427.
Scrima, et al., "Effects of Gamma-Hydroxybutyrate (GHB) on Narcolepsy-Cataplexy Symptoms and MSLT Results in Male and Female Patients", Association of Professional Sleep Societies, Abstract, 1988, 251.
Scrima, et al., "Gamma-Hydroxybutyrate Effects on Cataplexy and Sleep Attacks in Narcoleptics", Sleep Research, Abstract, 1987, 16: 134.
Scharf et al., "Effect of Gamma-Hydroxybutyrate on Pain, Fatigue, and the Alpha Sleep Anomaly in Patients with Fibromyalgia. Preliminary Report," The Journal of Rheumatology, 1998, 25:10, pp. 1986-1990.
International Searching Authority, "International Search Report, mailed Apr. 15, 2014, for International Patent Application No. PCT/US2013/074954."
International Searching Authority, "Written Opinion, mailed Apr. 15, 2014, for International Patent Application No. PCT/US2013/074954."

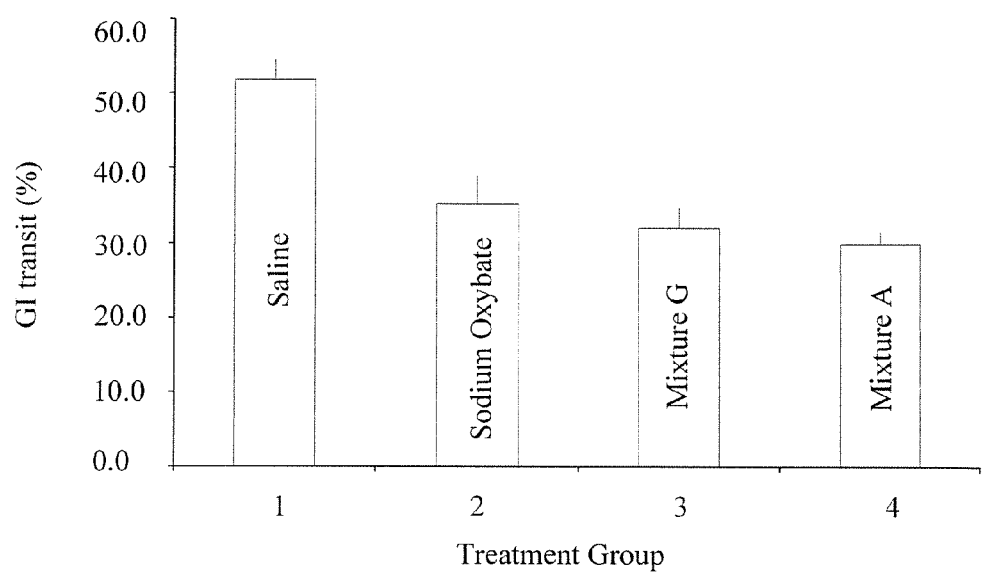

METHODS OF MAKING A MIXTURE OF SALTS OF GAMMA-HYDROXYBUTYRATE

1. CROSS REFERENCE

This application is a continuation of U.S. patent application Ser. No. 14/045,673, filed Oct. 3, 2013, which is a continuation of U.S. patent application Ser. No. 13/739,886, filed Jan. 11, 2013, which claims the benefit of U.S. Provisional Patent Application No. 61/737,695, filed Dec. 14, 2012, the content of each of which is hereby incorporated by reference in its entirety into this application.

2. FIELD OF THE INVENTION

Provided herein are pharmaceutical compositions and formulations comprising salts of gamma-hydroxybutyrate (GHB). In a preferred embodiment, the salts encompass more than one type of cation. Also provided herein are methods of making the pharmaceutical compositions and formulations, and methods of their use for the treatment of disorders including fibromyalgia and sleep disorders. Such sleep disorders include apnea, sleep time disturbances, narcolepsy, cataplexy, sleep paralysis, hypnagogic hallucination, sleep arousal, insomnia, and nocturnal myoclonus.

3. BACKGROUND OF THE INVENTION

Gamma-hydroxybutyrate (GHB), also known as "oxybate," is an endogenous compound with hypnotic properties that is found in many human body tissues. GHB is present, for example, in the mammalian brain and other tissues. In the brain, the highest GHB concentration is found in the hypothalamus and basal ganglia and GHB is postulated to function as a neurotransmitter (See Snead and Morley, 1981, *Brain Res.* 227(4): 579-89). The neurophamtacologic effects of GHB include increases in brain acetylcholine, increases in brain dopamine, inhibition of GAB A-ketoglutarate transaminase and depression of glucose utilization but not oxygen consumption in the brain. GHB treatment substantially reduces the signs and symptoms of narcolepsy, i.e., daytime sleepiness, cataplexy, sleep paralysis, and hypnagogic hallucinations. In addition, GHB increases total sleep time and REM sleep, and it decreases REM latency, reduces sleep apnea, and improves general anesthesia (see, e.g., U.S. Pat. Nos. 6,472,431; 6,780,889; 7,262,219; 7,851,506; 8,263,650; and 8,324,275; each of which is incorporated herein by reference in its entirety).

Sodium oxybate (Na.GHB), commerically sold as Xyrem®, is approved for the treatment of excessive daytime sleepiness and cataplexy in patients with narcolepsy. Na.GHB has also been reported to be effective for relieving pain and improving function in patients with fibromyalgia syndrome (See Scharf et al., 2003, *J. Rheumatol.* 30: 1070; Russell et al., 2009, *Arthritis. Rheum.* 60: 299), and in alleviating excessive daytime sleepiness and fatigue in patients with Parkinson's disease, improving myoclonus and essential tremor, and reducing tardive dyskinesia and bipolar disorder (See Ondo et al., 2008, *Arch. Neural.* 65: 1337; Frucht et al., 2005, *Neurology* 65: 1967; Berner, 2008, *J. Clin. Psychiatry* 69: 862).

Xyrem®, for use with patients with narcolepsy, is a chronically used product which requires high levels of the drug. The amount of sodium intake from the drug significantly increases the dietary sodium intake for patients, which is undesirable for patients with hypertension, heart disease, renal disease or at risk of stroke. Further, despite a general record of safety when used as prescribed, there are risks of abuse and misuse of Xyrem® which can cause serious medical problems, including seizures, loss of consciousness, coma, and death (see, e.g., FDA product label dated Nov. 13, 2006 for NDA no. 021196).

Little research has been done on salts of GHB, other than Na.GHB, and we are not aware of any combining multiple salts (see, e.g., U.S. Pat. Nos. 4,393,236; 4,983,632; 6,472, 431; Ferris and Went, 2012, *Forensic Science International* 216: 158-162).

Thus, there is a need for GHB formulations that minimize the undesirable side effects of the sodium, particularly in patients with hypertension, heart disease, renal disease or at risk of stroke, yet provide additional health benefits from the presence of the other salts. It is desireable that such modified formulations provide good solubility, stability and purity in order to provide safe, effective and consistent doses to patients, and also display acceptable phalinacodynamic and phalinacokinetic properties.

4. SUMMARY OF THE INVENTION

Provided herein are pharmaceutical compositions comprising salts of gamma-hydroxybutyrate (GHB) which are useful in the treatment of conditions responsive to GHB, for example, fibromyalgia and sleep disorders such as apnea, sleep time disturbances, narcolepsy, cataplexy, sleep paralysis, hypnagogic hallucination, sleep arousal, insomnia, and nocturnal myoclonus.

In certain embodiments, the pharmaceutical compositions provided herein are reduced in sodium content, which would render them particularly suitable for the treatment of patients with hypertension, heart disease, or renal disease, or who are at risk of stroke.

In one aspect, provided herein are pharmaceutical compositions comprising a mixture of salts of GHB, wherein the mixture comprises two or more salts selected from the group consisting of a sodium salt of hydroxybutyrate (Na.GHB), a potassium salt of gamma-hydroxybutyrate (K.GHB), a magnesium salt of gamma-hydroxybutyrate (Mg.(GHB)$_2$), and a calcium salt of gamma-hydroxybutyrate (Ca.(GHB)$_2$).

In certain embodiments, the pharmaceutical compositions comprise Na.GHB, K.GHB, Mg.(GHB)$_2$, and Ca.(GHB)$_2$. In certain embodiments, the Na.GHB salt is present in a wt/wt % of about 5% to about 10%, about 10% to about 15%, about 15% to about 20%, about 20% to about 25%, about 25% to about 30%, about 30% to about 35%, or about 35% to about 40%. In certain embodiments, the Na.GHB salt is present in a wt/wt % of about 5%, about 10%, about 15%, about 20%, about 25%, about 30%, about 35%, or about 40%. In certain embodiments, the K.GHB salt is present in a wt/wt % of about 10% to about 15%, about 15% to about 20%, about 20% to about 25%, about 25% to about 30%, about 30% to about 35%, or about 35% to about 40%. In certain embodiments, the K.GHB salt is present in a wt/wt % of about 10%, about 15%, about 20%, about 25%, about 30%, about 35%, or about 40%. In certain embodiments, the Mg.(GHB)$_2$ salt is present in a wt/wt % of about 5% to about 10%, about 10% to about 15%, about 15% to about 20%, about 20% to about 25%, or about 25% to about 30%. In certain embodiments, the Mg.(GHB)$_2$ salt is present in a wt/wt % of about 5%, about 10%, about 15%, about 20%, about 25%, or about 30%. In certain embodiments, the Ca.(GHB)$_2$ salt is present in a wt/wt % of about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, or about 75% to about 80%. In certain embodiments, the Ca.(GHB)$_2$ salt is present in a wt/wt % of about 20%, about 25%, about 30%, about 35%, about 40%, about 45%, about 50%, about 55%, about 60%, about 65%, about 70%, about 75%, or about 80%. In certain embodiments, the Na.GHB salt is present in a wt/wt % of about 5% to about 40%, the K.GHB salt is present in a wt/wt % of about 10% to about 40%, the Mg.(GHB)$_2$ salt is present in a wt/wt % of about 5% to about 30%, and the Ca.(GHB)$_2$ salt is present in a wt/wt % of about 20% to about 80%. In certain embodiments, the Na.GHB, K.GHB, Mg.(GHB)$_2$, and Ca.(GHB)$_2$ salts are present in a wt/wt % ratio of about 8%:32%:20%:40%, respectively. In certain embodiments, the Na.GHB, K.GHB, Mg.(GHB)$_2$, and Ca.(GHB)$_2$ salts are present in a wt/wt % ratio of about 29%:31%:13%:27%, respectively. In certain embodiments, the Na.GHB, K.GHB, Mg.(GHB)$_2$, and Ca.(GHB)$_2$ salts are present in a wt/wt % ratio of about 8%:23%:21%:48%, respectively.

In certain embodiments, the pharmaceutical composition comprises a mixture of any three of the salts selected from the group consisting of Na.GHB, K.GHB, Mg.(GHB)$_2$, and Ca.(GHB)$_2$.

In certain embodiments, the pharmaceutical composition comprises Na.GHB, K.GHB, and Ca.(GHB)$_2$. In certain embodiments, the Na.GHB salt is present in a wt/wt % of about 5% to about 40%, the K.GHB salt is present in a wt/wt % of about 10% to about 40%, and the Ca.(GHB)$_2$ salt is present in a wt/wt % of about 20% to about 80%. In certain embodiments, the Na.GHB, K.GHB, and Ca.(GHB)$_2$ salts are present in a wt/wt % ratio of about 11%:39%:50%, respectively.

In certain embodiments, the pharmaceutical composition comprises K.GHB, Mg.(GHB)$_2$, and Ca.(GHB)$_2$. In certain embodiments, the K.GHB salt is present in a wt/wt % of about 10% to about 50%, the Mg.(GHB)$_2$ salt is present in a wt/wt % of about 20% to about 60%, and the Ca.(GHB)$_2$ salt is present in a wt/wt % of about 10% to about 40%. In certain embodiments, the K.GHB, Mg.(GHB)$_2$, and Ca.(GHB)$_2$ salts are present in a wt/wt % ratio of about 33%:42%:25%, respectively.

In certain embodiments, the pharmaceutical composition comprises an aqueous solution of about 500 mg/mL of the mixture of salts of GHB, wherein the composition has a pH of about 7.0 to about 9.0, wherein the composition is chemically stable and resistant to microbial growth, and wherein the composition is free of preservatives. In certain embodiments, the pharmaceutical composition has a pH of about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In certain embodiments, the composition has a pH of about 7.0 to about 9.0, about 7.0 to about 8.5, about 7.3 to about 8.5, or about 7.5 to about 9.0. In certain embodiments, the composition has a pH of about 7.3 to about 8.5. In certain embodiments, the pharmaceutical composition additionally comprises a pH adjusting or buffering agent. In certain embodiments, the pH adjusting or buffering agent is an acid. In certain embodiments, the acid is an inorganic acid or an organic acid. In certain embodiments, the acid is selected from the group consisting of malic acid, citric acid, acetic acid, boric acid, lactic acid, hydrochloric acid, phosphoric acid, sulfuric acid, sulfonic acid, and nitric acid. In certain embodiments, the acid is malic acid.

In certain embodiments, the pharmaceutical composition is formulated as a liquid formulation. In certain embodiments, the formulation is chemically stable and resistant to microbial growth, and is free of preservatives. In certain embodiments, the level of gamma-butyrolacetone (GBL) is 0.1% or less of the formulation. In certain embodiments, the formulation is suitable for oral administration. In certain embodiments, the formulation additionally comprises a flavoring agent. In certain embodiments, the formulation is administered in a single or multiple dosage regimen.

In other aspects, provided herein are methods of treatment comprising administration of the pharmaceutical compositions or formulations disclosed herein.

In certain embodiments, the method treats cataplexy or daytime sleepiness in a patient who has been diagnosed with narcolepsy. In certain embodiments, the method treats conditions responsive to GHB, for example, fibromyalgia and sleep disorders such as apnea, sleep time disturbances, narcolepsy, cataplexy, sleep paralysis, hypnagogic hallucination, sleep arousal, insomnia, and nocturnal myoclonus. In certain embodiments, the patient who has been diagnosed with narcolepsy has also been diagnosed with hypertension, heart disease, renal disease, or is at risk of stroke.

In certain embodiments, the method comprises oral administration of the formulation in a multiple dosage regimen. In certain embodiments, the multiple dosage regimen comprises: (i) diluting an aqueous solution comprising about 500 mg/mL of the mixture of salts of gamma-hydroxybutyrate with an aqueous medium to provide a first dose of about 2.25 to about 4.5 grams of the mixture of salts; (ii) diluting an aqueous solution comprising about 500 mg/mL of the mixture of salts of gamma-hydroxybutyrate with an aqueous medium to provide a second dose of about 2.25 to about 4.5 grams of the mixture of salts; (iii) orally administering to a patient having narcolepsy the first dose within an hour prior to initial sleep onset; and (iv) orally administering to the patient having narcolepsy the second dose within 2.5 to 4 hours following initial sleep onset.

In certain embodiments, the multiple dosage regimen comprises: (i) diluting an aqueous solution comprising about 500 mg/mL of the mixture of salts of gamma-hydroxybutyrate with an aqueous medium to provide a first dose of about 1.0 to about 4.5 grams of the mixture of salts; (ii) diluting an aqueous solution comprising about 500 mg/mL of the mixture of salts of gamma-hydroxybutyrate with an aqueous medium to provide a second dose of about 1.0 to about 4.5 grams of the mixture of salts; (iii) orally administering to a patient having narcolepsy the first dose within an hour prior to initial sleep onset; and (iv) orally administering to the patient having narcolepsy the second dose within 2.5 to 4 hours following initial sleep onset.

In other aspects, provided herein are methods of making the pharmaceutical compositions disclosed herein.

In certain embodiments, the method of making comprises, for example, reacting GBL with one or more bases selected from the group consisting of sodium hydroxide, potassium hydroxide, magnesium hydroxide, and calcium hydroxide. In certain embodiments, the reaction is carried out in a single vessel. In certain embodiments, the reaction is carried out in multiple vessels and the product is subsequently combined.

5. BRIEF DESCRIPTION OF THE FIGURES

FIG. 1 provides the results of the gastrointestinal motility study in CD-1 mice for Saline, Xyrem® solution (Sodium Oxybate), and salt Mixtures A and G, which are disclosed in Examples 1 and 5, respectively.

6. DETAILED DESCRIPTION OF THE INVENTION

6.1 Definitions

As used herein, the term "gamma-hydroxybutyrate" (GHB) or "oxybate" refers to the negatively charged or anionic foal' (conjugate base) of gamma-hydroxybutyric acid. Without being limited by theory, GHB is believed to have the following structure:

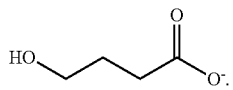

As used herein, the term "gamma-hydroxybutyric acid" refers to the protonated form (conjugate acid) of gamma-hydroxybutyrate. Without being limited by theory, gamma-hydroxybutyric acid is believed to have the following structure:

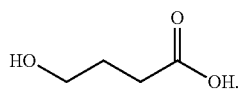

As used herein, the terms "sodium gamma-hydroxybutyrate" (Na.GHB) or "sodium oxybate" (Na.oxybate) refers to the sodium salt form of gamma-hydroxybutyric acid having the molecular weight of 126.09. Without being limited by any theory, Na.GHB is believed to have the following structure:

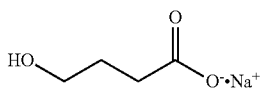

As used herein, the term "potassium gamma-hydroxybutyrate" (K.GHB) or "potassium oxybate" (K.oxybate) refers to the potassium salt foul of gamma-hydroxybutyric acid having the molecular weight of 142.19. Without being limited by any theory, K.GHB is believed to have the following structure:

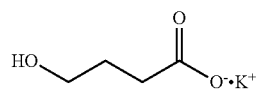

As used herein, the term "magnesium gamma-hydroxybutyrate" (Mg.(GHB)$_2$) or "magnesium oxybate" (Mg.oxybate) refers to the magnesium salt form of gamma-hydroxybutyric acid having the molecular weight of 230.50. Without being limited by theory, Mg.(GHB)$_2$ is believed to have the following structure:

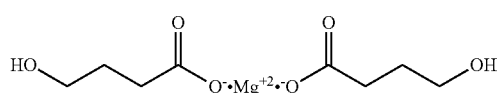

As used herein, the term "calcium gamma-hydroxybutyrate" (Ca.(GHB),) or "calcium oxybate" (Ca.oxybate) refers to the calcium salt foul of gamma-hydroxybutyric acid having the molecular weight of 246.27. Without being limited by theory, Ca.(GHB)$_2$ is believed to have the following structure:

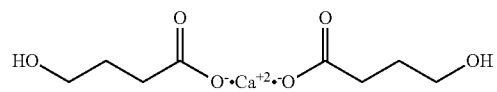

As used herein, the term "gamma-butyrolactone" (GBL) refers to a colorless oily liquid. Without being limited by theory, GBL is believed to have the following structure:

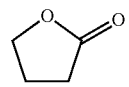

As used herein, the term "patient" refers to a mammal, particularly a human.

The terms "treat," "treating" or "treatment," as used herein, refer to a method of alleviating or abrogating a disease and/or its attendant symptoms.

As used herein, the term "about" or "approximately" means an acceptable error for a particular value as determined by those skilled in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

By "pharmaceutically acceptable" it is meant the active ingredient, cation, salt, diluent, excipient or carrier must be compatible with the other ingredients of the formulation and not unduly deleterious, for example, that the active ingredient, cation, salt, diluent, excipient or carrier does not produce an adverse, allergic or other untoward reaction, when administered to an animal, or a human, as appropriate.

The term "salt" or "salts," as used herein, refers to a compound formed by the interaction of an acid and a base, the hydrogen atoms of the acid being replaced by the positive ion or cation of the base. Pharmaceutically acceptable salts, include inorganic acids such as, for example, hydrochloric or phosphoric acids, or such organic acids as malic, acetic, oxalic, tartaric, mandelic, and the like. Salts formed can also be derived from inorganic bases such as, for example, sodium, potassium, silicates, ammonium, calcium, or ferric hydroxides, and such organic bases as isopropylamine, trimethylamine, histidine, procaine and the like. In certain preferred embodiments, the salt is formed from an inorganic base that is a metal, for example, an alkali metal, such as lithium, potassium, sodium, or the like, an alkaline earth metal, such as magnesium, calcium, barium, or the like, or aluminum or zinc. Other salts may comprise ammonium. Alkali metals, such as lithium, potassium, sodium, and the like, may be used, preferably with an acid to form a pH adjusting agent. Examples of pharmaceutically acceptable base addition salts include those derived from inorganic bases like sodium hydroxide, potassium hydroxide, magnesium hydroxide, calcium hydroxide, or ammonium hydroxide, and the like (See, e.g, Berge et al., 1977, *J. Pharm. Sci.* 66: 1).

As used herein, the terms "salt of GHB" or "salts of GHB," as used herein, refer to a compound formed by the interaction of gamma-hydroxybutyric acid (the conjugate acid of GHB) with a base, for example, NaOH, KOH, Mg(OH)$_2$, and Ca(OH)$_2$, and the like, the hydrogen atoms of the acid being replaced by the positive ion or cation of the base. Such salts may include, for example, Na.GHB, K.GHB, Mg.(GHB)$_2$, and Ca.(GHB)$_2$, and the like. It will be understood by those skilled in the art that such salts may be in solid form, or such salts may be in partially or fully solvated form, for example, as when dissolved in an aqueous medium. It will be further understood by those skilled in the art, that, depending on the solubility of the salt in the aqueous medium, that the salt may be present in the aqueous medium as solvated cation(s) and anion(s), or as a precipitated solid, as illustrated below for the solubility equilibrium of Ca.(GHB)$_2$:

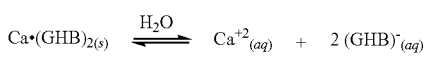

The terms "mixture of salts" or "salt mixture," as used herein, refers to salts of GHB where two or more different cations are present in combination with each other in a composition. Such mixtures of salts may include, for example, two or more salts selected from the group consisting of Na.GHB, K.GHB, Mg.(GHB)$_2$, and Ca.(GHB)$_2$.

The term "wt/wt %," are used herein, refers to the normalized weight percent of a particular salt in a salt mixture. A sample calculation of wt/wt % is provided in Example 1 of the present disclosure.

The term "wt/wt % ratio," as used herein, refers to the ratio of wt/wt % values in a mixture of salt. For example, where the salts Na.GHB, K.GHB, Mg.(GHB)$_2$, and Ca.(GHB)$_2$ are present in a wt/wt %'s of 8%, 32%, 20% and 40%, respectively, the wt/wt % ratio of Na.GHB, K.GHB, Mg.(GHB)$_2$, and Ca.(GHB)$_2$ in the mixture is 8%:32%:20%:40%.

The term, "buffering agent," as used herein, refers to a weak acid or base used to maintain the pH of a solution near a chosen pH value after the addition of another acidic or basic compound. The function of such an agent is to prevent the change in pH when acids or bases are added to a solution. Such agents may be acids, bases, or combinations thereof.

The term, "adjusting agent," as used herein, refers to an acid or base used to alter the pH of a solution to a chosen pH value. The function of such an agent is to alter the pH of a solution to the desired value subsequent to the addition of acidic or basic compounds.

The term, "acid," as used herein, refers to a substance which accepts a share in a pair of electrons. Such substances include malic acid, citric acid, acetic acid, boric acid, lactic acid, hydrochloric acid, phosphoric acid, sulfuric acid, sulfonic acid, nitric acid, and the like.

The term, "base," as used herein, refers to a substance which shares a pair of electrons. Such substances include sodium hydroxide, potassium hydroxide, magnesium hydroxide, calcium hydroxide, and the like.

The term, "chemically stable," as used herein, refers to a chemical compound which is not particularly reactive in a specific environment and retains its useful properties on a timescale of its expected usefulness. Specifically, the usefulness of the compound is maintained in the presence of air, moisture, or heat. Conversely, the compound lacks chemical stability if it decomposes under the conditions of a specific environment. As used herein in certain embodiments, "chemically stable" may mean resistant to degradation of GHB into its known or unknown decomposition elements. The level of GBL that is acceptable can be up to 0.15% of the formulation as per the ICH guidelines for shelf-life determination.

The term, "microbial," as used herein, refers to a microscopic organism that comprises either a single cell, cell cluster or multicellular organism.

The term "resistant to microbial growth" or "resistant to microbial challenge," as used herein, means that the compositions or formulations meet the criteria set by the Food and Drug Administration and the U.S. Pharmacopoeia for products made with aqueous bases or vehicles, which for bacteria means not less than a 1.0 log reduction from the initial count at 14 days, and no increase from the 14 days count at 28 days, and for yeast and molds, no increase from the initial calculated count at 14 and 28 days.

The term, "preservative," as used herein, refers to a naturally occurring or synthetically produced substance which can be added to food, pharmaceuticals, paints, biological samples, wood, etc. to prevent decomposition by microbial growth or by chemical decomposition.

The term, "formulation," as used herein, refers to a stable and pharmaceutically acceptable preparation of a pharmaceutical composition disclosed herein.

The term, "liquid formulation," as used herein, refers to a water-based formulation, in particular, a formulation that is an aqueous solution.

The term, "cataplexy," as used herein, refers to a condition where a patient exhibits a sudden and transient loss of muscle tone, often triggered by emotions.

The term, "daytime sleepiness," as used herein, refers to a condition where a patient exhibits persistent sleepiness, and often a general lack of energy, even after apparent adequate night time sleep.

The term, "narcolepsy," as used herein, refers to a chronic sleep disorder characterized by excessive sleepiness and sleep attacks at inappropriate times.

The term, "apnea," as used herein, refers to a condition where a patient suspends external breathing.

The term, "sleep time disturbances," as used herein, refers to a condition where a patient exhibits abnormal sleep patterns. Sleep time disturbances can be serious enough to interfere with normal physical, mental and emotional functioning.

The term, "sleep paralysis," as used herein, refers to a condition in which a patient who is falling asleep or awakening form sleep experience an inability to move. It is a transition state between wakefulness and rest characterized by complete muscle weakness.

The term, "hypnagogic hallucination," as used herein, refers to a transition state between wakefulness and sleep where a patient experiences vivid hallucinations.

The term, "sleep arousal," as used herein, refers to a condition where a patient engages in sexual acts while still asleep.

The term, "insomnia," as used herein, refers to a condition where a patient has difficulties falling asleep and maintaining sleep.

The term, "nocturnal myoclonus," as used herein, refers to a condition where a patient has repetitive movement of the limbs during sleep or even wakefulness which is sometimes confused with a seizure.

The term "flavoring" or "flavoring agent," as used herein, refers to a substance that alters the flavor of the composition during oral consumption. A type of "flavoring agent" would be a sweetener.

The term "coloring" or "coloring agent," as used herein, refers to a substance that alters the color of the composition.

6.2 Embodiments of the Invention 6.2.1 Pharmaceutical Compositions Comprising Salt Mixtures of GHB In certain aspects, provided herein are pharmaceutical compositions comprising gamma-hydroxybutyrate (GHB) and one or more pharmaceutically acceptable cations of an alkali metal or an alkaline earth metal. As used herein, "alkali metal" means any of the elements found in Group IA of the periodic table, including, for example, lithium, sodium, and potassium. As used herein, "alkaline earth metal" means any of the elements found in Group II of the periodic table, including, for example, magnesium and calcium.

In certain embodiments, the pharmaceutical compositions comprise GHB and more than one pharmaceutically acceptable cations of an alkali metal or an alkaline earth metal.

In certain embodiments, the pharmaceutical compositions comprise GHB and more than one cation selected from the group consisting of $Na^+$, $K^+$, $Mg^{+2}$, and $Ca^{+2}$. In certain embodiments, the pharmaceutical compositions comprise GHB and two or more cations selected from the group consisting of $Na^+$, $K^+$, $Mg^{+2}$, and $Ca^{+2}$. In certain embodiments, the pharmaceutical compositions comprise GHB and three or more cations selected from the group consisting of $Na^+$, $K^+$, $Mg^{+2}$, and $Ca^{+2}$. In certain embodiments, the pharmaceutical compositions comprise GHB and all four cations selected from the group consisting of $Na^+$, $K^+$, $Mg^{+2}$, and $Ca^{+2}$. In certain embodiments, the pharmaceutical compositions comprise GHB and more than one cation selected from the group consisting of $K^+$, $Mg^{+2}$, and $Ca^{+2}$. In certain embodiments, the pharmaceutical compositions comprise GHB and all three cations selected from the group consisting of $K^+$, $Mg^{+2}$, and $Ca^{+2}$. In certain embodiments, the pharmaceutical compositions do not comprise the cation $Na^+$, so as to minimize the undesirable side effects of the sodium, particularly in patients with hypertension, heart disease, renal disease or at risk of stroke. In certain embodiments, the pharmaceutical compositions do not comprise the cation $Na^+$, so as to improve the taste of the compositions.

In certain aspects, provided herein are pharmaceutical compositions comprising salts of GHB. As used herein, the term "salt of GHB" or "salts of GHB" is used interchangeably with the term "cation." For example, a pharmaceutical composition comprising GHB and the four cations $Na^+$, $K^+$, $Mg^{+2}$, and $Ca^{+2}$ will be understood by those skilled in the art to also mean a pharmaceutical composition comprising the salts Na.GHB, K.GHB, Mg.(GHB)$_2$, and Ca.(GHB)$_2$. It will be also understood by those skilled in the art that such salts may be in solid form, or may be in partially or fully solvated form, for example, as when dissolved in an aqueous medium. It will be further understood by those skilled in the art, that, depending on the solubility of the salt in the aqueous medium, that the salt may be present in the aqueous medium as solvated cation(s) and anion(s), or as a precipitated solid.

In certain embodiments, the pharmaceutical compositions comprise more than one salt selected from the group consisting of a sodium salt of hydroxybutyrate (Na.GHB), a potassium salt of gamma-hydroxybutyrate (K.GHB), a magnesium salt of gamma-hydroxybutyrate (Mg.(GHB)$_2$), and a calcium salt of gamma-hydroxybutyrate (Ca.(GHB)$_2$). In certain embodiments, the pharmaceutical compositions comprise two or more salts selected from the group consisting of Na.GHB, K.GHB, Mg.(GHB)$_2$, and Ca.(GHB)$_2$. In certain embodiments, the pharmaceutical compositions comprise three or more salts selected from the group consisting of Na.GHB, K.GHB, Mg.(GHB)$_2$, and Ca.(GHB)$_2$. In certain embodiments, the pharmaceutical compositions comprise all four salts selected from the group consisting of Na.GHB, K.GHB, Mg.(GHB)$_2$, and Ca.(GHB)$_2$. In certain embodiments, the pharmaceutical compositions comprise more than one salt selected from the group consisting of K.GHB, Mg.(GHB)$_2$, and Ca.(GHB)$_2$. In certain embodiments, the pharmaceutical compositions comprise all three salts selected from the group consisting of K.GHB, Mg.(GHB)$_2$, and Ca.(GHB)$_2$. In certain embodiments, the pharmaceutical compositions do not comprise the salt Na.GHB, so as to minimize the undesirable side effects of the sodium, particularly in patients with hypertension, heart disease, renal disease or at risk of stroke.

In certain embodiments, the pharmaceutical compositions comprise a mixture of more than one salt selected from the group consisting of Na.GHB, K.GHB, Mg.(GHB)$_2$, and Ca.(GHB)$_2$. In certain embodiments, the pharmaceutical compositions comprise a mixture or two or more salts selected from the group consisting of Na.GHB, K.GHB, Mg.(GHB)$_2$, and Ca.(GHB)$_2$. In certain embodiments, the pharmaceutical compositions comprise a mixture of three or more salts selected from the group consisting of Na.GHB, K.GHB, Mg.(GHB)$_2$, and Ca.(GHB)$_2$. In certain embodiments, the pharmaceutical composition comprises a mixture of the four salts Na.GHB, K.GHB, Mg.(GHB)$_2$, and Ca.(GHB)$_2$. In certain embodiments, the mixture of salts does not comprise the salt Na.GHB.

In certain embodiments, the pharmaceutical composition comprises a mixture of any three of the salts selected from the group consisting of Na.GHB, K.GHB, Mg.(GHB)$_2$, and Ca.(GHB)$_2$. In certain embodiments, the pharmaceutical composition comprises K.GHB, Mg.(GHB)$_2$, and Ca.(GHB)$_2$. In certain embodiments, the pharmaceutical composition comprises Na.GHB, Mg.(GHB)$_2$, and Ca.(GHB)$_2$. In certain embodiments, the pharmaceutical composition comprises Na.GHB, K.GHB, and Ca.(GHB)$_2$. In certain embodiments, the pharmaceutical composition comprises Na.GHB, K.GHB, and Mg.(GHB)$_2$.

In certain embodiments, the pharmaceutical composition comprises a mixture of any two of the salts selected from the group consisting of Na.GHB, K.GHB, Mg.(GHB)$_2$, and Ca.(GHB)$_2$. In certain embodiments, the pharmaceutical composition comprises Na.GHB and K.GHB. In certain embodiments, the pharmaceutical composition comprises Na.GHB and Mg.(GHB)$_2$. In certain embodiments, the pharmaceutical composition comprises Na.GHB and Ca.(GHB)$_2$. In certain embodiments, the pharmaceutical composition comprises K.GHB and Mg.(GHB)$_2$. In certain embodiments, the pharmaceutical composition comprises K.GHB and Ca.(GHB)$_2$. In certain embodiments, the pharmaceutical composition comprises Mg.(GHB)$_2$ and Ca.(GHB)$_2$.

6.2.2 Weight/Weight and Molar Equivalents Percents

In certain embodiments, the pharmaceutical composition comprises varying weight/weight percentages (wt/wt %) of Na.GHB, K.GHB, Mg.(GHB)$_2$, and Ca.(GHB)$_2$.

In certain embodiments, the Na.GHB salt is present in a wt/wt % of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the Na.GHB salt is present in a wt/wt % of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In certain embodiments, the Na.GHB salt is absent.

In certain embodiments, the K.GHB salt is present in a wt/wt % of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the K.GHB salt is present in a wt/wt % of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In certain embodiments, the K.GHB salt is absent.

In certain embodiments, the Mg.(GHB)$_2$ salt is present in a wt/wt % of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the Mg.(GHB)$_2$ salt is present in a wt/wt % of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In certain embodiments, the Mg.(GHB)$_2$ salt is absent.

In certain embodiments, the Ca.(GHB)$_2$ salt is present in a wt/wt % of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the Ca.(GHB)$_2$ salt is present in a wt/wt % of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In certain embodiments, the Ca.(GHB)$_2$ salt is absent.

In certain embodiments, where the pharmaceutical composition comprises a mixture of Na.GHB, K.GHB, Mg.(GHB)$_2$, and Ca.(GHB)$_2$, the Na.GHB salt is present in a wt/wt % of about 5% to about 10%, about 10% to about 15%, about 15% to about 20%, about 20% to about 25%, about 25% to about 30%, about 30% to about 35%, or about 35% to about 40%. In certain embodiments, where the pharmaceutical composition comprises a mixture of Na.GHB, K.GHB, Mg.(GHB)$_2$, and Ca.(GHB)$_2$, the Na.GHB salt is present in a wt/wt % of about 5%, about 10%, about 15%, about 20%, about 25%, about 30%, about 35%, or about 40%.

In certain embodiments, where the pharmaceutical composition comprises a mixture of Na.GHB, K.GHB, Mg.(GHB)$_2$, and Ca.(GHB)$_2$, the K.GHB salt is present in a wt/wt % of about 10% to about 15%, about 15% to about 20%, about 20% to about 25%, about 25% to about 30%, about 30% to about 35%, or about 35% to about 40%. In certain embodiments, where the pharmaceutical composition comprises a mixture of Na.GHB, K.GHB, Mg.(GHB)$_2$, and Ca.(GHB)$_2$, the K.GHB salt is present in a wt/wt % of about 10%, about 15%, about 20%, about 25%, about 30%, about 35%, or about 40%.

In certain embodiments, where the pharmaceutical composition comprises a mixture of Na.GHB, K.GHB, Mg.(GHB)$_2$, and Ca.(GHB)$_2$, the Mg.(GHB)$_2$ salt is present in a wt/wt % of about 5% to about 10%, about 10% to about 15%, about 15% to about 20%, about 20% to about 25%, or about 25% to about 30%. In certain embodiments, where the pharmaceutical composition comprises a mixture of Na.GHB, K.GHB, Mg.(GHB)$_2$, and Ca.(GHB)$_2$, the Mg.(GHB)$_2$ salt is present in a wt/wt % of about 5%, about 10%, about 15%, about 20%, about 25%, or about 30%.

In certain embodiments, where the pharmaceutical composition comprises a mixture of Na.GHB, K.GHB, Mg.(GHB)$_2$, and Ca.(GHB)$_2$, it is contemplated that the Mg.(GHB)$_2$ salt may be present in a wt/wt % of about 30% to about 40%, or about 40% to about 50%, or even higher. In certain embodiments, where the pharmaceutical composition comprises a mixture of Na.GHB, K.GHB, Mg.(GHB)$_2$, and Ca.(GHB)$_2$, it is contemplated that the Mg.(GHB)$_2$ salt may be present in a wt/wt % or about 35%, about 40%, or about 45%, about 50%, or even higher.

In certain embodiments, where the pharmaceutical composition comprises a mixture of Na.GHB, K.GHB, Mg.(GHB)$_2$, and Ca.(GHB)$_2$, the Ca.(GHB)$_2$ salt is present in a wt/wt % of about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, or about 70% to about 80%. In certain embodiments, where the pharmaceutical composition comprises a mixture of Na.GHB, K.GHB, Mg.(GHB)$_2$, and Ca.(GHB)$_2$, the Ca.(GHB)$_2$ salt is present in a wt/wt % of about 20%, about 25%, about 30%, about 35%, about 40%, about 45%, about 50%, about 55%, about 60%, about 65%, about 70%, about 75%, or about 80%.

In certain embodiments, where the pharmaceutical composition comprises a mixture of Na.GHB, K.GHB, Mg.(GHB)$_2$, and Ca.(GHB)$_2$, the Na.GHB salt is present in a wt/wt % of about 5% to about 40%, the K.GHB salt is present in a wt/wt % of about 10% to about 40%, the Mg.(GHB)$_2$ salt is present in a wt/wt % of about 5% to about 30%, and the Ca.(GHB)$_2$ salt is present in a wt/wt % of about 20% to about 80%.

In certain embodiments, where the pharmaceutical composition comprises a mixture of Na.GHB, K.GHB, Mg.(GHB)$_2$, and Ca.(GHB)$_2$, the Na.GHB, K.GHB, Mg.(GHB)$_2$, and Ca.(GHB)$_2$ salts are present in a wt/wt % ratio of about 8%:32%:20%:40%, respectively.

In certain embodiments, where the pharmaceutical composition comprises a mixture of Na.GHB, K.GHB, Mg.(GHB)$_2$, and Ca.(GHB)$_2$, the Na.GHB, K.GHB, Mg.(GHB)$_2$, and Ca.(GHB)$_2$ salts are present in a wt/wt % ratio of about 29%:31%:13%:27%, respectively.

In certain embodiments, where the pharmaceutical composition comprises a mixture of Na.GHB, K.GHB, Mg.(GHB)$_2$, and Ca.(GHB)$_2$, the Na.GHB, K.GHB, Mg.(GHB)$_2$, and Ca.(GHB), salts are present in a wt/wt % ratio of about 8%:23%:21%:48%, respectively.

In certain embodiments, where the pharmaceutical composition comprises a mixture of Na.GHB, K.GHB, and Ca.(GHB)$_2$, the Na.GHB salt is present in a wt/wt % of about 5% to about 40%, the K.GHB salt is present in a wt/wt % of about 10% to about 40%, and the Ca.(GHB)$_2$ salt is present in a wt/wt % of about 20% to about 80%.

In certain embodiments, where the pharmaceutical composition comprises a mixture of Na.GHB, K.GHB, and Ca.(GHB)$_2$, the Na.GHB salt is present in a wt/wt % of about 5% to about 40%, the K.GHB salt is present in a wt/wt % of about 20% to about 40%, and the Ca.(GHB)$_2$ salt is present in a wt/wt % of about 20% to about 60%.

In certain embodiments, where the pharmaceutical composition comprises a mixture of Na.GHB, K.GHB, and Ca.(GHB)$_2$, the Na.GHB, K.GHB, and Ca.(GHB)$_2$ salts are present in a wt/wt % ratio of about 11%:39%:50%, respectively.

In certain embodiments, where the pharmaceutical composition comprises a mixture of K.GHB, Mg.(GHB)$_2$, and Ca.(GHB)$_2$, the K.GHB salt is present in a wt/wt % of about 10% to about 50%, the Mg.(GHB)$_2$ salt is present in a wt/wt % of about 20% to about 60%, and the Ca.(GHB)$_2$ salt is present in a wt/wt % of about 10% to about 40%.

In certain embodiments, the K.GHB salt is present in a wt/wt % of about 10% to about 50%, the Mg.(GHB)$_2$ salt is present in a wt/wt % of about 20% to about 60%, and the Ca.(GHB)$_2$ salt is present in a wt/wt % of about 10% to about 40%.

In certain embodiments, where the pharmaceutical composition comprises a mixture of K.GHB, Mg.(GHB)$_2$, and Ca.(GHB)$_2$, the K.GHB, Mg.(GHB)$_2$, and Ca.(GHB)$_2$ salts are present in a wt/wt % ratio of about 33%:42%:25%, respectively.

In certain embodiments, the pharmaceutical compositions comprise varying percents of oxybate, expressed as % molar equivalents (% mol. equiv.) of Na.GHB, K.GHB, Mg.(GHB)$_2$, and Ca.(GHB)$_2$. The terms "% molar equivalents" and "% mol. equiv.," as used herein, refer to molar composition of salts expressed as a percent of GHB equivalents. Those skilled in the art will understand that as each GHB unit is considered to be one molar equivalent, the monovalent cations, Na$^+$ and K$^+$, have one molar equivalent per salt, and the divalent cations, Mg$^{+2}$ and Ca$^{+2}$, have two molar equivalents per salt. A sample calculation of % mol. equiv. is provided in Example 1 of the present disclosure.

In certain embodiments, the Na.GHB salt is present in a % mol. equiv. of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the Na.GHB salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, the K.GHB salt is present in a % mol. equiv. of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the K.GHB salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, the Mg.(GHB)$_2$ salt is present in a % mol. equiv. of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the Mg.(GHB)$_2$ salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, the Ca.(GHB)$_2$ salt is present in a % mol. equiv. of about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the Ca.(GHB)$_2$ salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, where the pharmaceutical composition comprises a mixture of Na.GHB, K.GHB, Mg.(GHB)$_2$, and Ca.(GHB)$_2$, the Na.GHB salt is present in a % mol. equiv. of about 5% to about 10%, about 10% to about 15%, about 15% to about 20%, about 20% to about 25%, about 25% to about 30%, about 30% to about 35%, or about 35% to about 40%. In certain embodiments, where the pharmaceutical composition comprises a mixture of Na.GHB, K.GHB, Mg.(GHB)$_2$, and Ca.(GHB)$_2$, the Na.GHB salt is present in a % mol. equiv. of about 5%, about 10%, about 15%, about 20%, about 25%, about 30%, about 35%, or about 40%.

In certain embodiments, where the pharmaceutical composition comprises a mixture of Na.GHB, K.GHB, Mg.(GHB)$_2$, and Ca.(GHB)$_2$, the K.GHB salt is present in a % mol. equiv. of about 10% to about 15%, about 15% to about 20%, about 20% to about 25%, about 25% to about 30%, about 30% to about 35%, or about 35% to about 40%. In certain embodiments, where the pharmaceutical composition comprises a mixture of Na.GHB, K.GHB, Mg.(GHB)$_2$, and Ca.(GHB)$_2$, the K.GHB salt is present in a % mol. equiv. of about 10%, about 15%, about 20%, about 25%, about 30%, about 35%, or about 40%.

In certain embodiments, where the pharmaceutical composition comprises a mixture of Na.GHB, K.GHB, Mg.(GHB)$_2$, and Ca.(GHB)$_2$, the Mg.(GHB)$_2$ salt is present in a % mol. equiv. of about 5% to about 10%, about 10% to about 15%, about 15% to about 20%, about 20% to about 25%, or about 25% to about 30%. In certain embodiments, where the pharmaceutical composition comprises a mixture of Na.GHB, K.GHB, Mg.(GHB)$_2$, and Ca.(GHB)$_2$, the Mg.(GHB)$_2$ salt is present in a % mol. equiv. of about 5%, about 10%, about 15%, about 20%, about 25%, or about 30%.

In certain embodiments, where the pharmaceutical composition comprises a mixture of Na.GHB, K.GHB, Mg.(GHB)$_2$, and Ca.(GHB)$_2$, it is contemplated that the Mg.(GHB)$_2$ salt may be present in a % mol. equiv. of about 30% to about 40%, or about 40% to about 50%, or even higher. In certain embodiments, where the pharmaceutical composition comprises a mixture of Na.GHB, K.GHB, Mg.(GHB)$_2$, and Ca.(GHB)$_2$, it is contemplated that the Mg.(GHB)$_2$ salt may be present in a % mol. equiv. of about 35%, about 40%, about 45%, or about 50%, or even higher.

In certain embodiments, where the pharmaceutical composition comprises a mixture of Na.GHB, K.GHB, Mg.(GHB)$_2$, and Ca.(GHB)$_2$, the Ca.(GHB)$_2$ salt is present in a % mol. equiv. of about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, or about 75% to about 80%. In certain embodiments, where the pharmaceutical composition comprises a mixture of Na.GHB, K.GHB, Mg.(GHB)$_2$, and Ca.(GHB)$_2$, the Ca.(GHB)$_2$ salt is present in a % mol. equiv. of about 20%, about 25%, about 30%, about 35%, about 40%, about 45%, about 50%, about 55%, about 60%, about 65%, about 70%, about 75%, or about 80%.

In certain embodiments, where the pharmaceutical composition comprises a mixture of Na.GHB, K.GHB, Mg.(GHB)$_2$, and Ca.(GHB)$_2$, the Na.GHB salt is present in a % mol. equiv. of about 5% to about 40%, the K.GHB salt is present in a % mol. equiv. of about 10% to about 40%, the Mg.(GHB)$_2$ salt is present in a % mol. equiv. of about 5% to about 30%, and the Ca.(GHB)$_2$ salt is present in a % mol. equiv. of about 20% to about 80%.

In certain embodiments, where the pharmaceutical composition comprises a mixture of Na.GHB, K.GHB, Mg.(GHB)$_2$, and Ca.(GHB)$_2$, the Na.GHB, K.GHB, Mg.(GHB)$_2$, and Ca.(GHB)$_2$ salts are present in a % mol. equiv. ratio of about 8%:28%:22%:41%, respectively.

In certain embodiments, where the pharmaceutical composition comprises a mixture of Na.GHB, K.GHB, Mg.(GHB)$_2$, and Ca.(GHB)$_2$, the Na.GHB, K.GHB, Mg.(GHB)$_2$, and Ca.(GHB)$_2$ salts are present in a % mol. equiv. ratio of about 29%:28%:15%:28%, respectively.

In certain embodiments, where the pharmaceutical composition comprises a mixture of Na.GHB, K.GHB, Mg.(GHB)$_2$, and Ca.(GHB)$_2$, the Na.GHB, K.GHB, Mg.(GHB)$_2$, and Ca.(GHB)$_2$ salts are present in a % mol. equiv. ratio of about 8%:23%:21%:48%, respectively.

In certain embodiments, where the pharmaceutical composition comprises a mixture of Na.GHB, K.GHB, and Ca.(GHB)$_2$, the Na.GHB salt is present in a % mol. equiv. of about 5% to about 40%, the K.GHB salt is present in a % mol. equiv. of about 10% to about 40%, and the Ca.(GHB)$_2$ salt is present in a % mol. equiv. of about 20% to about 80%.

In certain embodiments, where the pharmaceutical composition comprises a mixture of Na.GHB, K.GHB, and Ca.(GHB)$_2$, the Na.GHB, K.GHB, and Ca.(GHB)$_2$ salts are present in a % mol. equiv. ratio of about 11%:36%:53%, respectively.

In certain embodiments, where the pharmaceutical composition comprises a mixture of K.GHB, Mg.(GHB)$_2$, and Ca.(GHB)$_2$, the K.GHB salt is present in a % mol. equiv. of about 10% to about 50%, the Mg.(GHB)$_2$ salt is present in a % mol. equiv. of about 20% to about 60%, and the Ca.(GHB)$_2$ salt is present in a % mol. equiv. of about 10% to about 40%.

In certain embodiments, where the pharmaceutical composition comprises a mixture of K.GHB, Mg.(GHB)$_2$, and Ca.(GHB)$_2$, the K.GHB, Mg.(GHB)$_2$, and Ca.(GHB)$_2$ salts are present in a % mol. equiv. ratio of about 33%:42%:25%, respectively.

6.2.3 Concentrations and pH's

In certain embodiments, the pharmaceutical composition comprises an aqueous solution.

In certain embodiments, the concentration of the mixture of salts of GHB in the solution is about 100 to about 150 mg/mL, about 150 to about 200 mg/mL, about 200 to about 250 mg/mL, about 250 to about 300 mg/mL, about 300 to about 350 mg/mL, about about 350 to about 400 mg/mL, about 400 to about 450 mg/mL, about 450 to about 500 mg/mL, about 500 to about 550 mg/mL, about 550 to about 600 mg/mL, about 600 to about 650 mg/mL, about 650 to about 700 mg/mL, about 700 to about 750 mg/mL, about 750 to about 800 mg/mL, about 800 to about 850 mg/mL, or about 850 to about 900 mg/mL. In certain embodiments, the concentration of the mixture of salts of GHB in the solution is about 250 mg/mL to about 750 mg/mL. In certain embodiments, the concentration of the mixture of salts of GHB in the solution is about 150 mg/mL, about 200 mg/mL, about 250 mg/mL, about 300 mg/mL, about 350 mg/mL, about 400 mg/mL, about 450 mg/mL, about 500 mg/mL, about 550 mg/mL, about 600 mg/mL, about 650 mg/mL, about 700 mg/mL, about 750 mg/mL, about 800 mg/mL, about 850 mg/mL, or about 900 mg/mL. In certain embodiments, the concentration of the mixture of salts of GHB in the solution is about 500 mg/mL.

It will be understood that the maximum solubility of GHB is affected by the pH of the aqueous medium. For example, at about pH 4, the maximum amount of Na.GHB that can be dissolved is about 450 mg/ml. The value of pH that is conducive to GHB solubility increases so that the minimal pH that will dissolve 750 mg/ml GHB was found to be about pH 6.8.

Accordingly, in certain embodiments, the composition has a pH of about 3.5 to about 4.0, about 4.0 to about 4.5, about 4.5 to about 5.0, about 5.5 to about 6.0, about 6.0 to about 6.5, about 6.5 to about 7.0, about 7.0 to about 7.5, about 7.5 to about 8.0, about 8.0 to about 8.5, or about 8.5 to about 9.0. In certain embodiments, the composition has a pH of about 3.5, about 4.0, about 4.5, about 5.0, about 5.5, about 6.0, about 6.5, about 7.0, about 7.5, about 8.0, about 8.5, or about 9.0. In certain embodiments, the composition has a pH of about 7.0 to about 9.0, about 7.0 to about 8.5, about 7.3 to about 8.5, or about 7.5 to about 9.0. In certain embodiments, the composition has a pH of about 7.3 to about 8.5.

In certain embodiments, the composition is chemically stable and resistant to microbial growth. In certain embodiments, the composition is free of preservatives.

It will also be understood that the pH of the aqueous solution affects the resistance of the composition to microbial growth at about 500 mg/ml GHB. For example, Na.GHB at this concentration in an aqueous medium that is between about pH 5 and pH 9 is resistant to microbial growth, with compositions at about pH 6 to about pH 7.5 being particularly resistant to microbial growth. However, at concentrations of GHB greater than about 750 mg/ml above about pH 7.5, the resistance to microbial growth is reduced.

It will be further understood that the concentration of GHB in the composition, when evaluated in relationship to the pH, affects the resistance of the GHB composition to microbial challenge. For example, compositions of Na.GHB at or below 150 mg/ml are poorly resistant to microbial challenge from a pH range of about pH 3 to about pH 9. However, concentrations of Na.GHB of greater than about 150 mg/ml, up to about 1000 mg/ml of GHB, are believed to be suitably resistant to microbial contamination at these pH ranges.

It will be further understood that the chemical stability of GHB is affected by pH. Accordingly, the method for preparing GHB, as described herein, particularly as disclosed in the specific examples, varies with pH. GBL begins to form if the pH is about 6 or less. Compositions with a pH of greater than about 6.0 are preferred to produce chemically stable formulations of GHB. Thus, a preferred range to produce chemically stable GHB would be from about pH 6 to about pH 9. However, any pH or range of pH values where a clinically acceptable amount of GBL is produced is also contemplated as being preferred, and is encompassed by the present invention. The range of GBL could be regulatorily broadened with availability of sufficient toxicological data.

In certain embodiments, a pH adjusting or buffering agent may be added to the composition. The choice of a pH adjusting or buffering agent may affect the resistance to microbial challenge and/or the stability of GHB, as measured by the reduction in assayable GHB. Compositions of GHB, pH adjusted or buffered with malic acid are resistant to both microbial growth and chemical degradation of GHB, and are preferred. Other pH adjusting or buffering agents may be selected. Agents that adjust pH that are selected on this basis will undergo a taste testing study. However, any pH adjusting or buffering agent disclosed herein or as would be known to those skilled in the art is contemplated as being useful from the compositions or formulations disclosed herein. Of course, any salt, flavoring agent, excipient, or other pharmaceutically acceptable addition described herein or as would be known to those skilled in the art is contemplated as being useful for the compositions or formulations disclosed herein.

In certain embodiments, the pH adjusting or buffering agent is an acid. In certain embodiments, the pH adjusting or buffering agent is an inorganic acid or an organic acid. In certain embodiments, the pH adjusting or buffering agent is selected from the group consisting of malic acid, citric acid, acetic acid, boric acid, lactic acid, hydrochloric acid, phosphoric acid, sulfuric acid, sulfonic acid, and nitric acid. In certain embodiments, the pH adjusting or buffering agent is malic acid.

The aqueous solutions disclosed herein typically comprise an effective amount of GHB, which may be dissolved or dispersed in a pharmaceutically acceptable carrier and/or an aqueous medium.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Insofar as any conventional media or agent is incompatible with the active ingredient, its use in the therapeutic compositions is not appropriate. Supplementary compatible active ingredients can be incorporated into the compositions. For human administration, preparations should meet sterility, pyrogenicity, general safety and purity standards as required by the Food and Drug Administration (FDA).

6.2.4 Formulations

In certain embodiments, the compositions disclosed herein are provided in a formulation, preferably, a liquid formulation, although solid formulations are also contemplated.

In certain embodiments, the formulation is chemically stable and resistant to microbial growth. In certain embodiments, the formulation is free of preservatives. In certain embodiments, the level of gamma-butyrolacetone (GBL) is 0.1% or less of the formulation.

In certain embodiments, the formulation is suitable for oral administration.

In certain embodiments, the formulation additionally comprises a flavoring agent. Preferred sweeteners or flavoring agents would be microbially non-metabolizable. Especially preferred sweeteners or flavoring agents would be carbohydrates such as xylitol and sorbitol. Such flavoring agents include, but are not limited to, acacia syrup, anethole, anise oil, aromatic elixir, benzaldehyde, benzaldehyde elixir-compound, caraway, caraway oil, cardamom oil, cardamom seed, cardamom spirit, cardamom tincture-compound, cherry juice, cherry syrup, cinnamon, cinnamon oil, cinnamon water, citric acid, citric acid syrup, clove oil, coca, coca syrup, coriander oil, dextrose, eriodictyon, eriodictyon fluidextract, eriodictyon syrup-aromatic, ethyl acetate, ethyl, vanillin, fennel oil, ginger, ginger fluidextract, ginger oleoresin, glucose, glycerin, *glycyrrhiza*, *glycyrrhiza* elixir, *glycyrrhiza* extract, *glycyrrhiza* extract-pure, *glycyrrhiza* fluidextract, *glycyrrhiza* syrup, honey, non-alcoholic elixir, lavender oil, citrus extract or oil, lemon oil, lemon tincture, mannitol, methyl salicylate, nutmeg oil, orange-bitter-elixir, orange-bitter-oil, orange flower oil, orange flower water, orange oil, orange peel-bitter, orange-peel-sweet-tincture, orange spirit-compound, compound, orange syrup, peppermint, peppermint oil, peppermint spirit, peppermint water, phenylethyl alcohol, raspberry juice, raspberry syrup, rosemary oil, rose oil, rose water, saccharin, saccharin calcium, saccharin sodium, sarsaparilla syrup, sorbitol solution, spearmint, spearmint oil, sucralose, sucrose, syrup, thyme oil, tolu balsam, tolu balsam syrup, vanilla, vanilla tincture, vanillin or wild cherry syrup.

In certain embodiments, the formulation additionally comprises a coloring agent. Preferred coloring agents would be microbially non-metabolizable.

In certain embodiments, the formulation is administered in a single or multiple dosage regimen.

Any of the above formulations may be prepared and/or packaged as a powdered or dry form for mixing with an aqueous medium before oral administration, or they may be prepared in an aqueous medium and packaged. After mixing with an aqueous medium, preferably to prepare a solution, these formulations are resistant to both microbial growth and chemical conversion of GHB to GBL, thereby increasing the shelf-life of therapeutic formulations of GHB in an aqueous medium. These formulations then provide an easily titratable liquid medium for measuring the dosage of GHB to be administered to a patient. Additional embodiments of the composition and methods of preparation are described below and in the examples.

The GHB may be lyophilized for more ready formulation into a desired vehicle or medium where appropriate. The active compounds may be formulated for parenteral administration, e.g., formulated for injection via intravenous, intraarterial, intramuscular, sub-cutaneous, intralesional, intraperitoneal or other parenteral routes. The preparation of a composition that comprises an aqueous solution that contains a GHB agent as an active component or ingredient will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including, e.g., aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free acid or pharmacologically acceptable salts can be prepared in water suitably mixed with hydroxypropylcellulose and/or a pharmaceutically acceptable surfactant. Dispersions can also be prepared in glycerol, liquid polyethylene glycols, and mixtures thereof as well as in oils. Under ordinary conditions of storage and use, these preparation may best contain a preservative to further prevent the growth of microorganisms.

The carrier can also be a solvent or dispersion medium containing, for example, water, ethanol, polyol (for example, glycerol, propylene glycol, and liquid polyethylene glycol, or the like), suitable mixtures thereof, and vegetable oils. The proper fluidity can be maintained, for example, by the use of a substance, such as lecithin (e.g. a coating), by the maintenance of the required particle size in the case of dispersion and by the use of surfactants. The prevention of the action of microorganisms can be brought about by any of the preservatives described herein, or as would be known to those skilled in the art, including various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate.

Sterile injectable solutions are prepared by incorporating the active compounds in the required amount in the appropriate solvent with, various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent (although DMSO may not now be a permitted human drug) is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The active GHB may be formulated within a therapeutic mixture to comprise about 100 to about 10,000 milligrams per dose. Multiple doses can also be administered.

In addition to the compounds formulated for parenteral administration, such as intravenous or intramuscular injection, other pharmaceutically acceptable forms include, e.g., tablets or other solids; liposomal formulations; time release capsules; and any other form currently used, including creams, which then may be admixed with an aqueous medium for oral administration.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5, though other pH ranges disclosed herein the specific examples, such as pH 3 to about pH 9, or pH 6 to about 7.5, are contemplated. In addition, preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

The preferred oral formulations may include such normally employed excipients, as, for example, pharmaceutical grades of xylitol, mannitol, lactose, starch, magnesium stearate, sodium saccharin, cellulose, magnesium carbonate and the like. These compositions can take the form of solutions, suspensions, tablets, pills, capsules, sustained release formulations or powders to be admixed with an aqueous medium. In certain defined embodiments, oral pharmaceutical compositions will comprise an inert diluent or assimilable edible carrier, or they may be enclosed in hard or soft shell gelatin capsule, or they may be compressed into tablets, or the GHB may be packaged separately from or in combination with the excipients, salts, flavorings or any other components described herein, to be admixed with an aqueous medium for oral or injectable formulations, or they may be incorporated directly with the food (i.e. a beverage) of the diet.

For oral therapeutic administration, the active compounds may be incorporated with excipients and used in the form of tablets, buccal tablets or tabs, troches, capsules, elixirs, suspensions, syrups, wafers, and the like, to be admixed with an aqueous medium. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, natural as gum tragacanth, acacia, cornstarch, or gelatin or synthetic as polyvinyl acetate; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a natural or synthetic flavoring agent. When the dosage unit form is a capsule for admixing with a specific volume of an aqueous medium, it may contain, in addition to materials of the above type, a liquid carrier. Various other materials may be present as coatings or to otherwise modify the physical form of the dosage unit. For instance, tablets, pills, or capsules may be coated with sugar, natural or synthetic polymers, or both. A syrup or elixir may contain the active compounds, sucrose as a sweetening agent, a preservative, a dye and/or a flavoring.

Additionally, any excipient, salt, acid, pH-mediating, adjusting or buffering compound or agent, flavoring, solution, solvent, dispersion, glycerol, glycol, oil, antibacterial and antifungal agents, antibiotics and antihistamines, binders, disintegrating agents, lubricants, sweetening agents, or any other additive or ingredient from those enumerated above or in the examples, or in any pharmaceutically acceptable composition or carrier described herein, or as would be known by one of skill in the art, is contemplated for use in aqueous mediums or solid forms of the GHB compositions of the invention. One or more of these compositions may be packaged with GHB or packaged separately from GHB prior to consumption. If packaged separately, useful compositions of GHB may be obtained by mixing GHB with the other components with an aqueous medium prior to consumption. Such components may be packaged in a kit, described below.

Therapeutic kits of the present invention are kits comprising GHB. Such kits will generally contain, in suitable container, a pharmaceutically acceptable formulation of GHB. The kit may have a single container, or it may have distinct container for each component, or distinct container for various combinations of components.

When the components of the kit are provided in one or more liquid formulations, the liquid formulation is an aqueous medium, with a sterile aqueous solution being particularly preferred. The GHB compositions may also be formulated into a syringeable composition. In which case, the container means may itself be a syringe, pipette, vial, ampule or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, pouch syringe or other container means, into which the GHB formulation or components thereof are placed, preferably, suitably allocated. The kits may also comprise a second container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained.

In certain embodiments, the kits of the present invention contain one or more bottles of liquid formulation comprising GHB, two dosing cups with child-resistant caps, a liquid measuring device and a medication guide.

Irrespective of the number or type of containers, the kits of the invention may also comprise, or be packaged with, an instrument for assisting with the injection/administration or placement of the GHB composition within the body of an animal. Such an instrument may be a drinking cup, syringe, pipette, or any such medically approved delivery vehicle.

6.2.5 Methods of Treatment

The compositions and formulations comprising mixed salts of GHB, disclosed herein, are also contemplated to be useful in the treatment of any of these disorders or conditions in patients. GHB has also been used alone as a narcotic in patients with a terminal carcinomatous state. GHB has been used with other analgesics, neuroleptics, or with a subliminal barbiturate dose for use as an anesthesia. It is also contemplated that the GHB compositions and formulations disclosed herein may be used as a narcotic, hypnotic, or as a soporific. It is further contemplated that the GHB compositions and formulations comprising mixed salts of GHB, disclosed herein, may be used in combination with analgesics, neuroleptics or barbiturates for use as an anesthesia.

The GHB compositions and formulations comprising mixed salts of GHB, disclosed herein, may be prepared and administered by any of the means described herein, particularly those described in the section "Formulations" and the examples, or by any means as would be known to those of skill in the art.

Accordingly, in certain aspects, are methods of treatment comprising administration to a patient of the compositions or formulations comprising mixed salts GHB disclosed herein.

In certain embodiments, the compositions or formulations comprising mixed salts of GHB, disclosed herein, are useful in the treatment of cataplexy or daytime sleepiness in a patient who has been diagnosed with narcolepsy.

In certain embodiments, the compositions or formulations comprising mixed salts of GHB, disclosed herein, are useful in the treatment of conditions responsive to GHB, for example, sleep disorders such as apnea, sleep time disturbances, narcolepsy, cataplexy, sleep paralysis, hypnagogic hallucination, sleep arousal, insomnia, and nocturnal myoclonus.

In certain embodiments, the methods of treatment comprising administration of the compositions or formulations comprising mixed salts GHB disclosed herein.

In certain embodiments, the method comprises oral administration of the compositions or formulations comprising mixed salts GHB, disclosed herein, in a multiple dosage regimen.

In certain embodiments, the multiple dosage regimen comprises one or more steps, as follows: (i) diluting an aqueous solution comprising about 500 mg/mL of the mixture of salts of gamma-hydroxybutyrate with an aqueous medium to provide a first dose of about 1 to about 10 grams of the mixture of salts; (ii) diluting an aqueous solution comprising about 500 mg/mL of the mixture of salts of gamma-hydroxybutyrate with an aqueous medium to provide a second dose of about 1 to about 10 grams of the mixture of salts; (iii) orally administering to a patient having narcolepsy the first dose within an hour prior to initial sleep onset; and (iv) orally administering to the patient having narcolepsy the second dose within 2.5 to 4 hours following initial sleep onset.

In certain embodiments, the multiple dosage regimen comprises one or more steps, as follows: (i) diluting an aqueous solution comprising about 500 mg/mL of the mixture of salts of gamma-hydroxybutyrate with an aqueous medium to provide a first dose of about 2.25 to about 4.5 grams of the mixture of salts; (ii) diluting an aqueous solution comprising about 500 mg/mL of the mixture of salts of gamma-hydroxybutyrate with an aqueous medium to provide a second dose of about 2.25 to about 4.5 grams of the mixture of salts; (iii) orally administering to a patient having narcolepsy the first dose within an hour prior to initial sleep onset; and (iv) orally administering to the patient having narcolepsy the second dose within 2.5 to 4 hours following initial sleep onset.

In certain embodiments, the multiple dosage regimen comprises one or more steps, as follows: (i) diluting an aqueous solution comprising about 500 mg/mL of the mixture of salts of gamma-hydroxybutyrate with an aqueous medium to provide a first dose of about 1.0 to about 4.5 grams of the mixture of salts; (ii) diluting an aqueous solution comprising about 500 mg/mL of the mixture of salts of gamma-hydroxybutyrate with an aqueous medium to provide a second dose of about 1.0 to about 4.5 grams of the mixture of salts; (iii) orally administering to a patient having narcolepsy the first dose within an hour prior to initial sleep onset; and (iv) orally administering to the patient having narcolepsy the second dose within 2.5 to 4 hours following initial sleep onset.

In certain embodiments, the multiple dosage regimen comprises one or more steps, as follows: (i) diluting an aqueous solution comprising about 500 mg/mL of the mixture of salts of gamma-hydroxybutyrate with an aqueous medium to provide a first dose of about 4.5 to about 10 grams of the mixture of salts; (ii) diluting an aqueous solution comprising about 500 mg/mL of the mixture of salts of gamma-hydroxybutyrate with an aqueous medium to provide a second dose of about 4.5 to about 10 grams of the mixture of salts; (iii) orally administering to a patient having narcolepsy the first dose within an hour prior to initial sleep onset; and (iv) orally administering to the patient having narcolepsy the second dose within 2.5 to 4 hours following initial sleep onset.

In certain embodiments, the multiple dosage regimen comprises one or more steps, as follows: (i) diluting an aqueous solution comprising about 500 mg/mL of the mixture of salts of gamma-hydroxybutyrate with an aqueous medium to provide a first dose of about 3.0 to about 10 grams of the mixture of salts; (ii) diluting an aqueous solution comprising about 500 mg/mL of the mixture of salts of gamma-hydroxybutyrate with an aqueous medium to provide a second dose of about 3.0 to about 10 grams of the mixture of salts; (iii) orally administering to a patient having narcolepsy the first dose within an hour prior to initial sleep onset; and (iv) orally administering to the patient having narcolepsy the second dose within 2.5 to 4 hours following initial sleep onset.

It will be understood, however, that the specific dose level and frequency of dosage for any particular patient may be varied and will depend upon a variety of factors including: the metabolic stability and length of action, the age, body weight, general health, sex, diet, mode and time of administration, rate of excretion, drug combination, the severity of the particular condition, and the host undergoing therapy.

6.2.6 Methods of Making

In certain aspects, provided herein are methods of making the compositions or formulations comprising mixed salts GHB disclosed herein. Several different methods of making have been reported in the literature (see, e.g., U.S. Pat. Nos. 4,393,236; 4,983,632; 6,472,431; Ferris and Went, 2012, *Forensic Science International* 216: 158-162). Those skilled in the art will recognize that these methods can be incorporated in the making of the compositions or formulations comprising mixed salts GHB disclosed herein.

In certain embodiments, mixtures of GHB salts can be made by direct reaction of GBL with an aqueous mixture of one of more of the following bases: sodium hydroxide, potassium hydroxide, calcium hydroxide, and magnesium hydroxide. After reaction the mixture may then be filtered under mild vacuum.

In certain embodiments, a solvent, such as water, is used to dissolve the GHB salt mixture to a desired concentration, for example, by adjusting the amount of water in the mixture.

In certain embodiments, the concentration of a GHB salt solution is adjusted by concentrating the mixture using standard methods, such as evaporators, reverse osmosis, and similar techniques known to those skilled in the art.

In certain embodiments, the method of making comprises reacting gamma-butyrolacetone (GBL) with one or more bases selected from the group consisting of sodium hydroxide, potassium hydroxide, magnesium hydroxide, and calcium hydroxide.

In certain embodiments, the reaction is carried out in a single vessel. For example, a mixture of Na.GHB, K.GHB, Mg.(GHB)$_2$, and Ca.(GHB)$_2$ may be made by direct addition of GBL to in a single vessel containing an aqueous mixture of sodium hydroxide, potassium hydroxide, magnesium hydroxide, and calcium hydroxide.

In certain embodiments, the reaction is carried out in multiple vessels and the product is subsequently combined. For example, Ca.(GHB)) may be made by direct addition of GBL to aqueous sodium hydroxide, and the product combined with Mg.(GHB)$_2$.

In certain embodiments, the methods of making include methods of making the pharmaceutical compositions and formulations disclosed herein.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

7. EXAMPLES

7.1 Example 1: Synthesis of Mixture A

For Mixture A, 34.38 g of 99.9% GBL were charged, which is $(34.38 \times 0.999/68.089 \times 1000) = 399.0$ mMol. The total base equivalents charged were 404.40 mEq. Hence, the excess base was $((404.40-399.0)/(399.0 \times 100\%)) = 1.35\%$.

TABLE 1

Example calculation

| Base | Base MW | Purity | Grams Amount | Base mMols | Stoich. Ratio | Base mEQ | % molar equiv GHB | Salt | Salt MW | Salt mass grams | Salt wt/wt % | Conc mg/ml |
|---|---|---|---|---|---|---|---|---|---|---|---|---|
| NaOH | 40.00 | 98.50% | 1.398 | 34.43 | 1 | 34.43 | 8.5% | Na•GHB | 126.09 | 4.34 | 8.5% | 42.61 |
| KOH | 56.11 | 86.72% | 7.337 | 113.40 | 1 | 113.40 | 28.0% | K•GHB | 142.20 | 16.12 | 31.4% | 158.29 |
| Ca(OH)$_2$ | 74.10 | 99.00% | 6.268 | 83.74 | 2 | 167.49 | 41.4% | Ca•(GHB)$_2$ | 246.27 | 20.62 | 40.2% | 202.46 |
| Mg(OH)$_2$ | 58.32 | 99.50% | 2.611 | 44.55 | 2 | 89.09 | 22.0% | Mg•(GHB)$_2$ | 230.50 | 10.27 | 20.0% | 100.80 |
| Total | | | 17.614 | 276.11 | | 404.40 | 100.0% | | | 51.36 | 100.0% | 504.17 |

| | |
|---|---|
| Base | Each of four bases used in this example |
| Base MW | Molecular weight of the base |
| Purity | Purity provided by manufacturer. It is assumed that impurities are non-reactive. |
| Gram Amount | Amount, in grams, of each base charged to the reaction |
| Base mMols | Corresponding amount, in millimoles, of pure base (that is, Purity × Gram-Amount × 1000/Base-MW) |
| Stoichiometry Ratio | The number of GHB moles reacted with each mole of base |
| Base mEQ | Base equivalents for reaction with GHB (that is, Base-mMols × Stiochiometry-Ratio). This is also the Oxybate or GHB equivalents value. |
| % molar equiv GHB | Molar composition of salts expressed as Percent of Oxybate Equivalents |
| Salt | The oxybate salt species |
| Salt MW | Molecular weight of the oxybate salt |
| Salt-mass-grams | Mass of salt produced by reaction (that is, Base-mMols × Salt-MW/1000) |
| Salt wt/wt % | Normalized weight percent |
| Conc (mg/ml) | Concentration in mg/ml equivalent to a 3.97M Na-GHB solution (500 mg/ml sodium oxybate). That is, 3.97 × (% equiv-GHB) × (Salt-MW)/(Stoich. Ratio) |

The following synthetic examples provide exemplary syntheses of mixture of oxybate salts. Alternate methods of synthesizing mixtures of oxybate salts, including methods of synthesizing additional salts of oxybate are described below; still other alternate synthetic methods will be apparent to those skilled in the art.

Mixture A of Table 2 was arrived by direct reaction of GBL with an aqueous mixture of four bases. Sodium hydroxide (Sigma Aldrich Reagent, 98.50% assay), potassium hydroxide (Sigma Aldrich ACS Reagent, 86.72% assay), calcium hydroxide (Sigma Aldrich ACS Reagent, 99.0% assay), and magnesium hydroxide (Sigma Aldrich Reagent, 99.5% assay) were weighed as 1.398 grams, 7.337 grams, 6.268 grams, and 2.611 grams, respectively, into a 100 ml Pyrex volumetric flask. To this, 68.03 grams of water (ultrapure by reverse osmosis) was added with mixing and subsequently allowed to cool. GBL (99.9% purity) was added in 1 ml aliquots for a total of 34.38 grams. During addition, reaction occured immediately and heat was evolved. With cooling, the temperature did not exceed 80° C. After GBL addition, the mixture was placed in a temperature-controlled water bath kit to 80° C. with mixing, and allowed to react to completion in about 3 hours. The mixture was then filtered under mild vacuum, cooled to room temperature, and characterized for final pH, assay (by titration), solids content (by loss on drying), and purity (by reverse-phase gradient HPLC). The pH was 8.04, assay was 100.8% of target, solids content was 42.25%, and impurities consisted of un-reacted GBL (0.169%) and hydroxybutyl butyric acid (HBBA, 0.083%). The filtered solution was clear. The details of this and the mixtures of Examples 2-5 (including, e.g., Mixtures B-G) are provided in Tables 1-6.

Example calculations of molar equivalents and % wt/wt for salt mixtures are shown below for Mixture A in Table 1.

TABLE 2

Reaction Mixture (grams)

| Mixture | NaOH | KOH | MgOH$_2$ | CaOH$_2$ | GBL | Water | Total |
|---|---|---|---|---|---|---|---|
| A | 1.398 | 7.337 | 2.611 | 6.268 | 34.38 | 68.03 | 120.0 |
| B | 1.792 | 9.383 | 0.0 | 8.039 | 34.5 | 66.38 | 120.1 |
| C | 0.000 | 0.000 | 5.9 | 0.000 | 17.22 | 36.87 | 60.0 |
| D | — | — | — | — | — | — | — |
| E | 11.206 | 58.611 | 21.713 | 50.272 | 276.7 | 538.70 | 957.2 |
| F | 1.404 | 7.352 | 2.612 | 6.276 | 34.33 | 68.00 | 120.0 |
| G | 4.805 | 7.33 | 1.759 | 4.225 | 34.45 | 67.52 | 120.1 |

TABLE 3

Concentration of Oxybate salt (wt/wt %)

| Mixture | Na•GHB | K•GHB | Mg•GHB$_2$ | Ca•GHB$_2$ | Total |
|---|---|---|---|---|---|
| A | 8.45 | 31.40 | 19.99 | 40.16 | 100.0 |
| B | 10.57 | 39.18 | 0.00 | 50.24 | 100.0 |
| C | 0.00 | 0.00 | 100.00 | 0.00 | 100.0 |
| D | 8.47 | 31.36 | 19.97 | 40.22 | 100.0 |
| E | 8.40 | 31.09 | 20.61 | 39.92 | 100.0 |
| F | 8.49 | 31.42 | 19.97 | 40.14 | 100.0 |
| G | 28.79 | 31.07 | 13.34 | 26.80 | 100.0 |

TABLE 4

Concentration of Oxybate Salt (mg/mL)

| Mixture | Na·GHB | K·GHB | Mg·GHB$_2$ | Ca·GHB$_2$ | Total |
|---------|--------|-------|-----------|-----------|-------|
| A | 42.6 | 158.3 | 100.8 | 202.5 | 504.2 |
| B | 54.7 | 202.7 | 0 | 259.9 | 517.3 |
| C | 0 | 0 | 457.5 | 0 | 457.5 |
| D | 42.7 | 158.1 | 100.7 | 202.8 | 504.2 |
| E | 42.3 | 156.6 | 103.8 | 201.1 | 503.7 |
| F | 42.8 | 158.4 | 100.7 | 202.4 | 504.2 |
| G | 146.5 | 158.1 | 67.9 | 136.4 | 508.9 |

TABLE 5

Concentration of Oxybate Salt (molar equiv.)

Percent of oxybate (molar equiv.)

| Mixture | Na·GHB | K·GHB | Mg·GHB$_2$ | Ca·GHB$_2$ | Total |
|---------|--------|-------|-----------|-----------|-------|
| A | 8.5 | 28.0 | 22.0 | 41.4 | 100.0 |
| B | 10.9 | 35.9 | 0.0 | 53.2 | 100.0 |
| C | 0.0 | 0.0 | 100.0 | 0.0 | 100.0 |
| D | 8.5 | 28.0 | 22.0 | 41.5 | 100.0 |
| E | 8.4 | 27.7 | 22.7 | 41.1 | 100.0 |
| F | 8.5 | 28.1 | 22.0 | 41.4 | 100.0 |
| G | 29.2 | 28.0 | 14.8 | 27.9 | 100.0 |

TABLE 6

Results and Characterization of Formulas

| Mixture | Reaction Time (h) | Yield (%) | Base Excess | pH | Titration Assay (% target) | LOD % Solids | HPLC Area % GBL | Impurities HBBA |
|---------|------|------|------|------|-------|-------|-------|-------|
| A | 3 | 93 | 1.3 | 8.04 | 100.8 | 42.25 | 0.169 | 0.083 |
| B | 3 | 94 | 0.8 | 8.47 | 100.3 | 42.87 | 0.075 | 0.038 |
| C | 3 | 90 | 1.0 | 6.62 | 96.8 | 35.87 | 0.652 | 0.270 |
| D | — | — | — | 8.05 | 99.6 | 41.30 | 0.189 | 0.097 |
| E | 6.5 | 95 | 1.6 | 8.16 | 103.3 | 41.91 | 0.201 | 0.052 |
| F | 3.5 | 90 | 1.6 | 8.00 | 101.5 | 41.97 | 0.167 | 0.131 |
| G | 3.5 | 88 | 1.1 | 8.27 | 97.6 | 41.06 | 0.143 | 0.061 |

7.2 Example 2: Synthesis of Mixture B

Mixture B, containing sodium, potassium, calcium, but not magnesium, was also arrived by direct reaction of GBL with an aqueous mixture of the bases. Separately, magnesium oxybate (Mixture C) was made in the same molar strength by reaction of GBL with an aqueous suspension of magnesium hydroxide. The latter reaction was considerably slower, and especially slow as the reaction neared completion and most of the magnesium hydroxide was depleted. Both batches were then filtered. The two mixtures were then combined in a ratio of 0.78:0.22 (v/v) to arrive at Mixture D which is the same composition as Mixture A. Product made in this "2-pot" method has properties comparable to that of the "1-pot" method, but in some circumstances may be preferred.

7.3 Example 3: Synthesis of Mixture E

Mixture E was produced at approximately 8-fold larger batch size in a 1-liter vessel. The bases were weighed into the vessel, and water was quickly added with stirring. The temperature rose from 21° C. to 40° C. and was allowed to cool to 23° C. by immersion in a cold water bath. The vessel was then removed from cooling, and GBL was then added in 10 g aliquots while recording temperature. The temperature rose steadily with each aliquot of GBL added until between 75% and 79% addition, at which time the temperature began to fall slowly despite GBL addition, due to cooling. This phenomenon was consistent with the relatively fast reactions of sodium, potassium, and calcium hydroxides, and the much slower reaction of magnesium hydroxide, as the latter was about 23% by stoichiometry. After GBL addition, the vessel was then placed in a water bath controlled to 80° C. After 6.5 hours, the product was filtered and characterized for pH, assay, solids content, and purity.

7.4 Example 4: Synthesis of Mixture F

Although it is generally more convenient to add the GBL to a stirred mixture of bases in water, the reverse addition order produced a comparable product. In producing Mixture F, GBL was first loaded into a 100 ml reaction vessel. Separately, an aqueous mixture of the four bases was prepared with stirring, and this mixture was then added to the GBL in 1 ml aliquots. The reaction mixture was then placed in a 80° C. water bath for 3.5 hours, recovered after filtration, and characterized for pH, assay, % solids, and purity. The results are generally comparable to those of Mixture A, which was produced using the opposite order of addition.

7.5 Example 5: Synthesis of Mixture G

Mixture G was arrived by direct addition of gamma butyrolactone (GBL) to an aqueous mixture of the four bases. After GBL addition, the mixture was placed in a temperature-controlled water bath kit to 80° C. with mixing, and allowed to react to completion in about 3.5 hours. The mixture was then filtered under mild vacuum, cooled to room temperature, and characterized for final pH, assay (by titration), solids content (by loss on drying), and purity (by reverse-phase gradient HPLC). The pH was 8.27, assay was 97.6% of target, solids content was 41.06%, and impurities consisted of unreacted GBL (0.143%) and hydroxybutyl butyric acid (HBBA, 0.061%). The filtered solution was clear.

7.6 Example 6: Synthesis of Mixtures H and I

The oxybate salt mixture composition can be adjusted to produce a mixture having the same overall mass potency as sodium oxybate. In other words, the weighted-average molecular weight per molar equivalent of oxybate is the same (126.09). Thus, the absolute dosing of the oxybate salt mixture, in grams of drug substance, is the same as sodium oxybate. This is particularly useful for avoiding potential confusion and reducing medication errors as a result of switching patients from a sodium oxybate product to a mixed salt product. In other words, 6.0 grams dosing of sodium oxybate is also 6.0 grams dosing of the salt mixture. This feature cannot be achieved in alternative single-salts of oxybate.

Two such formulations were produced by the similar procedure as outlined in Example 1. Sodium hydroxide (Sigma Aldrich Reagent, 98.20% assay), potassium hydroxide (Sigma Aldrich ACS Reagent, 86.72% assay), calcium hydroxide (Sigma Aldrich ACS Reagent, 99.0% assay), and magnesium hydroxide (Sigma Aldrich Reagent, 99.5% assay) were weighed as indicated in Table 7, respectively, into a 100 ml Pyrex bottle. To this, water (ultrapure by reverse osmosis) was added with mixing, and finally GBL (99.9% purity) was added in about 2 ml aliquots. During addition, reaction occured immediately and heat was evolved. After GBL addition, the mixture was placed in a temperature-controlled water bath kit to 80° C. with mixing, and allowed to react to completion. After four hours, the conversion from reaction was about 99.5% and 98.5% (as measured by residual GBL). To speed completion, a small amount of magnesium hydroxide was added. After 5.25 hours, the mixtures were then filtered under mild vacuum and cooled to room temperature. The filtered solutions were clear. The solutions were characterized for final pH, assay by titration, solids content by evaporation at 150° C. (4 h) followed by equilibration at 60° C., and purity by reverse-phase gradient HPLC. The molecular weight per oxybate equivalent of each mixture was calculated from the assay and solids content results, and were in reasonable agreement with sodium oxybate (127.0 and 126.4 g/mol-equiv vs. 126.09 for sodium oxybate).

TABLE 7

Conditions and Results

|  | Mixture H | Mixture I |
|---|---|---|
| Target Formula (% molar equiv): | | |
| Na-GHB | 8.0% | 0.0% |
| K-GHB | 23.0% | 33.0% |
| Ca-(GHB)$_2$ | 48.0% | 25.0% |
| Mg-(GHB)$_2$ | 21.0% | 42.0% |
| Amounts charged (grams): | | |
| NaOH | 1.329 | 0 |
| KOH | 6.007 | 8.623 |
| Ca(OH)$_2$ | 7.268 | 3.776 |
| Mg(OH)$_2$ | 2.495 | 4.977 |
| GBL | 34.35 | 34.41 |
| Water | 68.4 | 68.3 |
| Additional Mg(OH)$_2$ to finish rxn | 0.46 g | 1.155 g |
| Product characterization: | | |
| pH | 8.22 | 8.41 |
| Oxybate assay (mEq/g) | 3.192 | 3.117 |
| Solids content (%) | 40.54 | 39.41 |
| MW per oxybate (g/Eq) | 127.0 | 126.4 |
| (As % of SXB MW) | 100.7 | 100.3 |
| Impurities: | | |
| GBL | 0.08 | 0.07 |
| HBBA | Not found | Not found |

7.7 Example 7: Gastrointestinal Motility Study

This example demonstrates that the pharmaceutical compositions comprising mixed salts of oxybate, disclosed herein, display acceptable pharmacokinetic properties (measured as GastroIntestinal transit rates), similar to those of Xyrem®.

In this study, Saline, Xyrem® solution (Sodium Oxybate), and two formulations (comprising Mixtures A and G, corresponding to Examples 1 and 5, respectively; hereafter referred to as "mixed salt formulations" in Example 7) were dosed orally, followed by oral administration of non-absorbable marker, Carmine, into male CD-1 mice. Following dosing, the small intestine, from the pylorus to the cecum, was removed. The distance the marker compound traveled was measured and calculated as a percentage of the total length of the small intestine. The animals in Groups 2 through 4 showed lethargy after receiving the test compounds. The animals in Group 1 showed normal activity during the study. The details of the study are provided below and are summarized in Table 8.

1.0 Objective: Evaluation of the GI motility of Xyrem® (Sodium Oxybate) and two other mixed salt formulations after oral administration in a male CD-1 mouse GI motility model~dosing and sampling only.

2.0 Experimental:
a. Materials
  i. The test compounds were provided by Jazz Pharmaceuticals, 3180 Porter Drive, Palo Alto, Calif. 94304.
  ii. Male CD-1 mice were obtained from Hilltop Lab Animals, Scottdale, Pa. 15683.
b. Dosing Solution Preparation
  All dosing solutions were prepared fresh on the day of dosing and were dosed within one hour of preparation.
c. Animal Dosing
  i. Animals were housed five per cage. All mice were identified by a cage label and tail mark. A single room was used for this study.
  ii. The animals were healthy at the start of the study. The mice, ranged in weight from 25 to 31 g.
  iii. The duration of acclimation was two days.
  iv. Animals were supplied with water and a commercial rodent diet ad libitum prior to the study initiation. Food was withheld from the animals for a minimum of twelve hours before the study and during the study. Water was supplied ad libitum.
  v. The animals were assigned randomly to treatment groups upon arrival.
  vi. The study was not blinded.
  vii. Animals were dosed via the appropriate route at time 0 on the appropriate day.
d. Sample Collection
  At 20 minutes post Carmine dose, the mice were euthanized and the small intestine from the pylorus to the cecum was removed. The distance the marker compound traveled was measured and calculated as a percentage of the total length of the small intestine.

TABLE 8

Study Design

| Treatment Group | Test Compound | Dosing Route | Animals N = | Dose mg/kg | Dosing Solution Conc. mg/mL (Sodium Oxybate Molar Equivalent basis) | Dosing Volume mL/kg | Vehicle | Sampling Time Point |
|---|---|---|---|---|---|---|---|---|
| 1* | NA | PO | 10 | NA | NA | 5 | Saline | 20 minutes post marker compound dose |

TABLE 8-continued

Study Design

| Treatment Group | Test Compound | Dosing Route | Animals N = | Dose mg/kg | Dosing Solution Conc. mg/mL (Sodium Oxybate Molar Equivalent basis) | Dosing Volume mL/kg | Vehicle | Sampling Time Point |
|---|---|---|---|---|---|---|---|---|
| 2* | Xyrem ® solution (Sodium Oxybate) | PO | 10 | 200 | 40 | 5 | Sterile Water | 20 minutes post marker compound dose |
| 3* | Mixture G | PO | 10 | 200 | 40 | 5 | Sterile Water | 20 minutes post marker compound dose |
| 4* | Mixture A | PO | 10 | 200 | 40 | 5 | Sterile Water | 20 minutes post marker compound dose |

*20 minutes after test compound dose, 6% Carmine (w/v) in 0.5% methyl cellulose, low viscosity in tap water was administered PO at 0.3 mL/mouse (Carai et al., Life Sciences 70 (2002) 3059-3067). Mice were sacrificed 20 minutes after this second dose.

Salt Mixtures:

| | | Percent of oxybate (molar equiv.) | | | |
|---|---|---|---|---|---|
| Treatment Group | Mixture | Na•GHB | K•GHB | Ca•(GHB)$_2$ | Mg•(GHB)$_2$ |
| 3 | G | 29.2% | 28.0% | 28.0% | 14.8% |
| 4 | A | 8.5% | 28.0% | 41.5% | 21.9% |

3.0 Results:

a. Observations

Animals receiving the Xyrem® solution and two other mixed salt formulations orally, showed lethargy. The animals in Group 1 showed normal activity during the study.

b. Data

See Table 9 and FIG. 1.

TABLE 9

Results

Group 1, Saline

| Mouse # | 1 | 2 | 3 | 4 | 5 | 6 | 7 | 8 | 9 | 10 | Mean | SEM |
|---|---|---|---|---|---|---|---|---|---|---|---|---|
| small intestine length (cm) | 41.5 | 38.0 | 42.0 | 32.0 | 36.0 | 38.0 | 35.5 | 39.5 | 33.5 | 36.5 | 37.3 | 1.0 |
| marker traveled (cm) | 22.0 | 25.0 | 18.0 | 17.0 | 16.0 | 21.5 | 21.5 | 14.5 | 18.5 | 18.0 | 19.2 | 1.0 |
| GI transit (%) | 53.0 | 65.8 | 42.9 | 53.1 | 44.4 | 56.6 | 60.6 | 36.7 | 55.2 | 49.3 | 51.8 | 2.7 |

Group 2, Xyrem ® solution (Sodium Oxybate)

| Mouse # | 11 | 12 | 13 | 14 | 15 | 16 | 17 | 18 | 19 | 20 | | |
|---|---|---|---|---|---|---|---|---|---|---|---|---|
| small intestine length (cm) | 38.0 | 31.5 | 37.0 | 37.5 | 32.0 | 38.0 | 37.5 | 42.0 | 36.0 | 40.5 | 37.0 | 1.0 |
| marker traveled (cm) | 11.0 | 10.5 | 9.5 | 9.0 | 16.0 | 21.0 | 7.5 | 12.0 | 16.5 | 16.0 | 12.9 | 1.3 |
| GI transit (%) | 28.9 | 33.3 | 25.7 | 24.0 | 50.0 | 55.3 | 20.0 | 28.6 | 45.8 | 39.5 | 35.1 | 3.8 |

Group 3, Salt Mixture G

| Mouse # | 21 | 22 | 23 | 24 | 25 | 26 | 27 | 28 | 29 | 30 | | |
|---|---|---|---|---|---|---|---|---|---|---|---|---|
| small intestine length (cm) | 42.5 | 39.0 | 39.0 | 32.0 | 38.5 | 38.0 | 32.5 | 39.0 | 40.0 | 37.5 | 37.8 | 1.0 |
| marker traveled (cm) | 10.5 | 16.0 | 14.0 | 10.5 | 6.5 | 10.5 | 11.5 | 9.0 | 17.0 | 15.0 | 12.1 | 1.1 |
| GI transit (%) | 24.7 | 41.0 | 35.9 | 32.8 | 16.9 | 27.6 | 35.4 | 23.1 | 42.5 | 40.0 | 32.0 | 2.7 |

TABLE 9-continued

Results

Group 4, Salt Mixture A

| Mouse # | 31 | 32 | 33 | 34 | 35 | 36 | 37 | 38 | 39 | 40 | | |
|---|---|---|---|---|---|---|---|---|---|---|---|---|
| small intestine length (cm) | 38.0 | 36.0 | 36.0 | 35.0 | 38.5 | 41.0 | 40.0 | 38.0 | 40.0 | 38.0 | 38.1 | 0.6 |
| marker traveled (cm) | 8.0 | 10.0 | 12.0 | 12.0 | 11.0 | 13.0 | 14.0 | 10.5 | 8.5 | 14.0 | 11.3 | 0.7 |
| GI transit (%) | 21.1 | 27.8 | 33.3 | 34.3 | 28.6 | 31.7 | 35.0 | 27.6 | 20.3 | 36.8 | 29.7 | 1.7 |

4.0 Conclusions: Saline, Xyrem® solution (Sodium Oxybate), and two other mixed salt formulations were dosed orally, followed by oral administration of non-absorbable marker, Cattnine, into male CD-1 mice. At 20 minutes post-Carmine dose, the mice were euthanized and the small intestine from the pylorus to the cecum was removed. The distance the marker compound traveled was measured and calculated as a percentage of the total length of the small intestine. Test compound treated groups showed lower transit rate compared to the control (saline) group; whereas Mixtures A and G displayed transit rates similar to those of Xyrem®.

7.8 Example 8: Microbial Challenge and Stability Testing of Formulations

This example provides protocols for microbial challenge and stability testing of the formulations disclosed herein.

1.0 Objective: To prepare, test and evaluate multiple formulations using alternative mixed salts of gamma-hydroxybutyrate.

2.0 Experimental:
a. Preparation
  Method for preparation of various formulations: For a one liter quantity of product, add the mixture of salts of GHB in 500 ml of purified and stir until dissolved. Prepare a 10% solution of the acid (Malic or Citric) and add slowly to the solution. The solution should be monitored for pH and temperature and both variables recorded at reasonable intervals (every 10 or 15 minutes). When the target pH is attained, the solution will be Q. S. to 1 liter, and pH rechecked and recorded. The final solutions will be filtered through 10 μm filters and 200 mL dispensed into 5 amber PET bottles with closures. Two bottles are used for microbial challenge studies and the remaining bottles are used for the limited stability evaluation.
b. Testing
  Formulations are tested by two methods of evaluation:
  i. Limited stability evaluation: (1) Storage Conditions: 25° C. (2) Pull Points: Day 0 (day of preparation), and day 28 (3) Testing Requirements: appearance (visual), potency (HPLC), impurities (HPLC) and pH.
  ii. Microbial challenge: (1) Storage Conditions: Microbial challenge studies of above formulations are set up with 5 microorganisms and stored for 28 days at 20-25° C., per USP <51> Eighth Supplement. (2) Microorganisms: After a sufficient quantity of each formulation is prepared, aliquots are inoculated with 5 microorganisms at a concentration of at least $10^5$ microorganisms/cc: (a) *Escherichia coli*, ATCC 8739 (b) *Pseudomonas aeruginosa*, ATCC 9027 (c) *Staphylococcus aureus*, ATCC 6538 (d) *Aspergillus niger*, ATCC 18404 (e) *Candida albicans*, ATCC 10231. (3) Time Points: A determination of the viable cell concentration in each inoculated container is performed after 0, 1, 3, 7, 14, 21 and 28 days.

3.0 Results:
i. Limited stability evaluation: Formulations are determined to be chemically stable if the level of GBL is 0.15% or less of the formulation as per the ICH guidelines for shelf-life determination.
ii. Microbial challenge: Formulations are determined to "Pass or Fail" based upon the USP criteria for perservative effectiveness which states: For Bacteria, "Not less than 1 log reduction from the initial microbial count at 14 days and no increase from the 14 days count at 28 days"; and for yeast and molds, "No increase from the initial calculated count at 14 and 28 days." Solutions which met these criteria are designated as "Pass" and those that do not meet these criteria are designated as "Fail".

7.9 Example 9: Preparation of Pharmaceutical Compositions Comprising a Mixture of Salts of GHB This example provides exemplary pharmaceutical compositions comprising mixtures of salts of GHB.

Pharmaceutical Composition Comprising Mixture A: A pharmaceutical composition is prepared according to Example 1. The pharmaceutical composition comprises Na.GHB, K.GHB, Mg.(GHB)$_2$, and Ca.(GHB)$_2$ salts in a wt/wt % ratio of about 8%:32%:20%:40%, respectively, at a total concentration of about 500 mg/mL. The pH of the composition is measured to be about 8.0. No preservatives are added to the composition. The composition is tested according to the protocols of Example 8 and is found to be chemically stable and resistant to microbial growth.

Pharmaceutical Composition Comprising Mixture B: A pharmaceutical composition is prepared according to Example 2. The pharmaceutical composition comprises Na.GHB, K.GHB, and Ca.(GHB)$_2$ salts in a wt/wt % ratio of about 11%:39%:50% respectively, at a total concentration of about 500 mg/mL. The pH of the composition is measured to be about 8.5. No preservatives are added to the composition. The composition is tested according to the protocols of Example 8 and is found to be chemically stable and resistant to microbial growth.

Pharmaceutical Composition Comprising Mixture G: A pharmaceutical composition is prepared according to Example 5. The pharmaceutical composition comprises Na.GHB, K.GHB, Mg.(GHB)$_2$, and Ca.(GHB)$_2$ salts in a wt/wt % ratio of about 29%:31%:13%:27%, respectively, at a total concentration of about 500 mg/mL. The pH of the composition is measured to be about 8.3. No preservatives are added to the composition. The composition is tested according to the protocols of Example 8 and is found to be chemically stable and resistant to microbial growth.

Pharmaceutical Composition Comprising Mixture H: A pharmaceutical composition is prepared according to Example 6. The pharmaceutical composition comprises Na.GHB, K.GHB, Mg.(GHB)$_2$, and Ca.(GHB)$_2$ salts in a wt/wt % ratio of about 8%:23%:21%:48%, respectively, at a total concentration of about 500 mg/mL. The pH of the composition is measured to be about 8.3. No preservatives are added to the composition. The composition is tested according to the protocols of Example 8 and is found to be chemically stable and resistant to microbial growth.

Pharmaceutical Composition Comprising Mixture I: A pharmaceutical composition is prepared according to Example 6. The pharmaceutical composition comprises K.GHB, Mg.(GHB)$_2$, and Ca.(GHB)$_2$ salts in a wt/wt % ratio of about 33%:42%:25%, respectively, at a total concentration of about 500 mg/mL. The pH of the composition is measured to be about 8.3. No preservatives are added to the composition. The composition is tested according to the protocols of Example 8 and is found to be chemically stable and resistant to microbial growth.

All publications and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those skilled in the art in light of the teachings of the specification that certain changes and modifications may be made thereto without departing from the spirit or scope of the appended claims.

What is claimed is:

1. A method of making a mixture of two or more salts of gamma-hydroxybutyrate (GHB), the method comprising:
   contacting gamma-butyrolactone (GBL) with two or more bases selected from the group consisting of sodium hydroxide (NaOH), potassium hydroxide (KOH), magnesium hydroxide (Mg(OH)$_2$), and calcium hydroxide (Ca(OH)$_2$), in a single reaction vessel under conditions sufficient to produce a mixture of two or more salts selected from the group consisting of a sodium salt of gamma-hydroxybutyrate (Na.GHB), a potassium salt of gamma-hydroxybutyrate (K.GHB), a magnesium salt of gamma-hydroxybutyrate (Mg.(GHB)$_2$), and a calcium salt of gamma-hydroxybutyrate (Ca.(GHB)$_2$).

2. The method of claim 1, wherein the GBL is contacted with four bases selected from the group consisting of NaOH, KOH, Mg(OH)$_2$, and Ca(OH)$_2$.

3. The method of claim 1, wherein the GBL is contacted with three bases selected from the group consisting of NaOH, KOH, Mg(OH)$_2$, and Ca(OH)$_2$.

4. The method of claim 3, wherein the GBL is contacted with KOH, Mg(OH)$_2$, and Ca(OH)$_2$.

5. The method of claim 1, wherein the GBL is contacted with two bases selected from the group consisting of KOH, Mg(OH)$_2$, and Ca(OH)$_2$.

6. The method of claim 1, wherein the contacting comprises addition of the GBL to the bases.

7. The method of claim 1, wherein the contacting comprises addition of the bases to the GBL.

8. The method of claim 1, wherein the conditions sufficient to produce the mixture comprise placing the reaction vessel in a water bath controlled to 80° C. for at least 3 hours.

9. The method of claim 1, further comprising filtering the mixture.

10. The method of claim 1, wherein the weighted average molecular weight per molar equivalent of the mixture of salts is about 126.09.

11. The method of claim 1, further comprising adding one or more of a buffering agent, a sweetening agent, a flavoring agent or a coloring agent, optionally in a pharmaceutically acceptable carrier.

12. A method of making a mixture of two or more salts of GHB, the Method comprising:
   contacting GBL with two or more bases selected from the group consisting of NaOH, KOH, Mg(OH)$_2$, and Ca(OH)$_2$, in two reaction vessels under conditions sufficient to produce a mixture of two or more salts selected from the group consisting of Na.GHB, K.GHB, Mg.(GHB)$_2$, and Ca.(GHB)$_2$;
   wherein the GBL is contacted with Mg(OH)$_2$ in the first reaction vessel, and
   wherein the GBL is contacted with one or more of NaOH, KOH, and Ca(OH)$_2$ in the second reaction vessel.

13. The method of claim 12, wherein the mixture comprises Mg.(GHB)$_2$ and Ca.(GHB)$_2$.

14. The method of claim 12, wherein the GBL is contacted with three bases selected from the group consisting of NaOH, KOH, Mg(OH)$_2$, and Ca(OH)$_2$.

15. The method of claim 14, wherein the GBL is contacted with KOH, Mg(OH)$_2$, and Ca(OH)$_2$.

16. The method of claim 12, wherein the contacting comprises addition of the GBL to the bases.

17. The method of claim 12, wherein the contacting comprises addition of the bases to the GBL.

18. A method of making a mixture of four salts of GHB, the method comprising:
   contacting GBL with four bases selected from the group consisting of NaOH, KOH, Mg(OH)$_2$, and Ca(OH)$_2$, in a single reaction vessel under conditions sufficient to produce a mixture of four salts selected from the group consisting of Na.GHB, K.GHB, Mg.(GHB)$_2$, and Ca.(GHB)$_2$.

19. The method of claim 18, wherein the contacting comprises addition of the GBL to the bases.

20. The method of claim 18, wherein the contacting comprises addition of the bases to the GBL.

21. The method of claim 18, wherein the conditions sufficient to produce the mixture comprise placing the reaction vessel in a water bath controlled to 80° C. for at least 3 hours.

22. The method of claim 18, further comprising filtering the mixture.

23. The method of claim 18, wherein the reaction vessel having has at least a one liter capacity.

24. The method of claim 18, wherein the weighted average molecular weight per molar equivalent of the mixture of salts is about 126.09.

25. The method of claim 18, further comprising adding one or more of a buffering agent, a sweetening agent, a flavoring agent or a coloring agent, optionally in a pharmaceutically acceptable carrier.

* * * * *